(12) United States Patent
de Almeida Moreira et al.

(10) Patent No.: US 8,231,895 B2
(45) Date of Patent: Jul. 31, 2012

(54) TARGETED DELIVERY TO HUMAN DISEASES AND DISORDERS

(75) Inventors: João Nuno Sereno de Almeida Moreira, Coimbra (PT); Vera Lúcia Dantas Nunes Caldeira de Moura, Coimbra (PT); Sérgio Paulo de Magalhães Simões, Coimbra (PT); Maria da Conceição Monteiro Pedroso de Lima, Coimbra (PT)

(73) Assignees: Universidade de Coimbra, Coimbra (PT); Centro de Neurociencias e Biologia Celular, Coimbra (PT)

( * ) Notice: Subject to any disclaimer, the term of this patent is extended or adjusted under 35 U.S.C. 154(b) by 439 days.

(21) Appl. No.: 12/153,649

(22) Filed: May 22, 2008

(65) Prior Publication Data

US 2009/0291049 A1 Nov. 26, 2009

(51) Int. Cl.
*A61K 9/12* (2006.01)
(52) U.S. Cl. ........................................ 424/450
(58) Field of Classification Search ........................ None
See application file for complete search history.

(56) References Cited

U.S. PATENT DOCUMENTS

| 2005/0196343 | A1* | 9/2005 | Reddy et al. | ............... | 424/9.322 |
| 2005/0287122 | A1 | 12/2005 | Bartlett et al. | | |

FOREIGN PATENT DOCUMENTS

| JP | 2008162981 A | 7/2008 |
| WO | 03/087124 A2 | 10/2003 |
| WO | 2007/055561 A1 | 5/2007 |
| WO | 2009/005793 A2 | 1/2009 |
| WO | 2010/008876 A2 | 1/2010 |

OTHER PUBLICATIONS

Maria E. Akerman, et al.; Nanocrystal targeting in vivo; PNAS; Oct. 1, 2002; vol. 99; No. 20; pp. 12617-12621.
Kimmo Porkka, et al; A fragment of the HMGN2 protein homes to the nuclei of tumor cells and tumor endothelial cells in vivo; PNAS; May 28, 2002; vol. 99; No. 11; pp. 7444-7449.
Tatsuhiro Ishida, et al.; Development of pH-sensitive liposomes that efficiently retain encapsulated doxorubicin (DXR) in blood; International Journal of Pharmaceutics 309 (2006); pp. 94-100.
T. Ishida, et al.; Targeted delivery and triggered release of liposomal doxorubicin enhances cytotoxicity against human B lymphoma cells; Biochimica et Biophysica Acta 1515 (2001); pp. 144-158.
Baselga, J. et al., "The epidermal growth factor receptor as a target for therapy in breast carcinoma." Breast Cancer Res Treat 29(1): 127-138 (1994).
Bowers, G. et al,, "The relative role of ErbB1-4 receptor tyrosine kinases in radiation signal transduction responses of human carcinoma cells." Oncogene 20(11): 1388-1397 (2001).
Daenen, L.G. et al., "Low-dose metronomic cyclophosphamide combined with vascular disrupting therapy induces potent antitumor activity in preclinical human tumor xenograft models." Mol. Cancer Ther. 8(10): 2872-2881 (2009).

Ishida, T. et al., "Targeted delivery and triggered release of liposomal doxorubicin enhances cytotoxicity against human B lymphoma cells." Biochim. Biophys. Acta 1515(2): 144-158 (2001).
Ishida, T. et al., "Development of pH-sensitive liposomes that efficiently retain encapsulated doxorubicin (DXR) in blood." Int J Pharm 309(1-2): 94-100 (2006).
Lee, E.S. et al., "Recent progress in tumor pH targeting nanotechnology." J. Control. Release 132(3): 164-170 (2008).
Lengyel, E. et al., "C-Met overexpression in node-positive breast cancer identities patients with poor clinical outcome independent of Her2/neu." Int. J. Cancer 113(4): 678-682 (2005).
Maeda, H., et al., "Mechanism of tumor-targeted delivery of macromolecular drugs, including the EPR effect in solid tumor and clinical overview of the prototype polymeric drug SMANCS." J Control Release 74(1-3): 47-61 (2001).
Moreira, J.N. et al, "Targeting Stealth liposomes in a murine model of human small cell lung cancer." Biochim. Biophys. Acta 1515(2): 167-176 (2001).
Moreira, J.N. et al., "A growth factor antagonist as a targeting agent for sterically stabilized liposomes in human small cell lung cancer." Biochim. Biophys. Acta 1514(2): 303-317 (2001).
Porkka, K. et al., "A fragment of the HMGN2 protein homes to the nuclei of tumor cells and tumor endothelial cells in vivo." Proc. Natl. Acad. Sci. USA 99(11): 7444-7449 (2002).
Siemann, D.W. et al., "Vascular targeted therapies in oncology." Cell Tissue Res 335(1): 241-248 (2009).
Simões, S. et al., "On the formulation of pH-sensitive liposomes with long circulation times." Adv. Drug Deliv. Rev. 56(7): 947-965 (2004).
Derfus et al. "Targeted quantum dot conjugates for siRNA delivery", *Bioconjugate Chem* 2007; pp. 1391-1396, vol. 18, No. 5.
Henke et al. "Peptide-conjugated antisense oligonucleotides for targeted inhibition of a transcriptional regulator in vivo", *Nature Biotechnology* 2008, pp. 91-100, vol. 26, No. 1.
Makela et al. "Peptide-mediated interferences with baculovirus transduction", *Journal of Biotechnology* 2008, pp. 20-32, vol. 134, No. 1-2.
Park et al. "Micellar hybrid nanoparticles for simultaneous magnetofluorescent imaging and drug delivery", *Angew. Chem, Int. Ed* 2008, pp. 7284-7288, vol. 47, No. 38.
Park et al. "Systematic surface engineering of magnetic nanoworms for in vivo tumor targeting", *Wiley-VCH Verlag GmbH & Co. KgaA, Weinheim* 2009, pp. 694-700, vol. 5, No. 6.

* cited by examiner

*Primary Examiner* — Sheela J Huff
(74) *Attorney, Agent, or Firm* — Wolf, Greenfield & Sacks, P.C.

(57) ABSTRACT

The present invention provides a system presenting site-specific accumulation through a ligand that specifically targets a receptor overexpressed on the surface of specific cells within a target organ, like, for example, tumor cells and/or vascular cells of tumor blood vessels. Moreover, this invention provides a method where, upon internalization of the previous-mentioned system by the target cells, triggered release at a high rate of the associated agent takes place, permitting efficient intracellular delivery and, thus, increased concentration of the transported cargo at the target site. Overall, this invention provides a method for the diagnosis, prevention and treatment of human diseases and disorders.

12 Claims, 8 Drawing Sheets
(8 of 8 Drawing Sheet(s) Filed in Color)

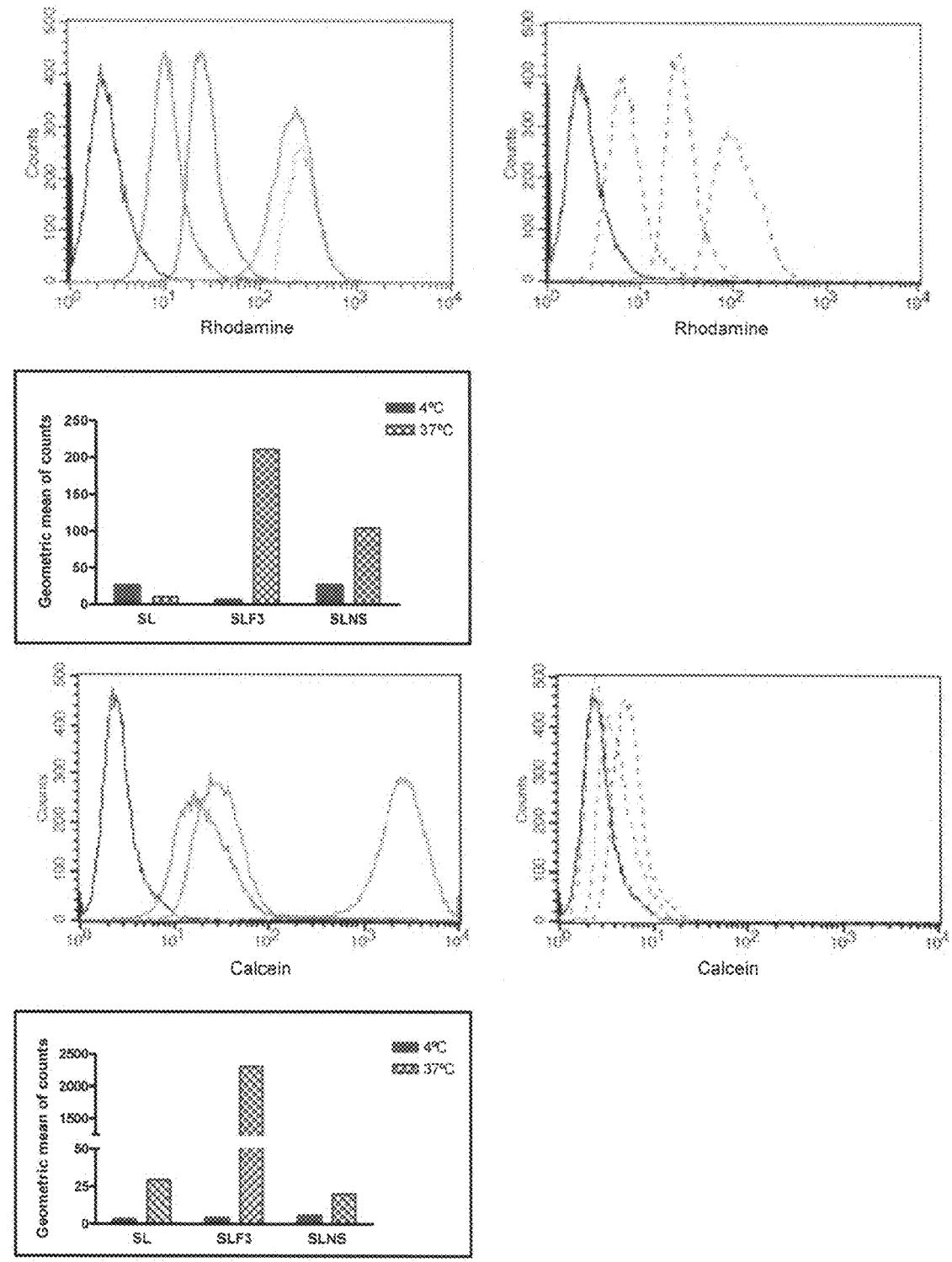

SEQUENCE LISTING

```
<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 2
<211> LENGTH: 10
<212> TYPE: PRT
<213> ORGANISM: Artificial
<220> FEATURE:
<223> OTHER INFORMATION: non-specific synthetic oligopeptide

<400> SEQUENCE: 2

Ala Arg Ala Leu Pro Ser Gln Arg Ser Arg
1               5                   10
```

TARGETED DELIVERY TO HUMAN DISEASES AND DISORDERS

BACKGROUND OF THE INVENTION

1. Field of the Invention

The present invention relates to the fields of human diseases and disorders, more specifically to methods of selectively homing and delivering an agent to human cells, combining targeting specificity with intracellular triggered release of the payload. The present invention can be applied, for example, in the treatment and/or diagnosis of different types of cancer as well as other diseases and disorders.

2. Background Information

Amongst human diseases and disorders, cancer is the leading cause of death throughout the western world. Even though, in most cases, diagnosis is often followed by surgery and the prognosis is favourable, recurrent forms often appear after surgery, indicating that metastases were already present by the time the disease was detected. This is the major obstacle for a complete remission of the tumor.

Traditional chemotherapy constitutes one of the most important treatment modalities against cancer. Chemotherapeutic agents, upon systemic administration, are generally characterized by a high volume of distribution that leads to a poor selectivity towards tumor cells and accumulation in healthy tissues. Such pattern of distribution can lead to increased toxicities against normal tissues that also show enhanced proliferative rates, such as the bone marrow, gastrointestinal tract and hair follicles. Myelosuppression, alopecia or mucositis are some of the most unpleasant and undesired consequences of fighting cancer with conventional therapy (Ferrara, 2005). Side effects that occur as a result of toxicities to normal tissues mean that anticancer chemotherapeutics are often given at sub-optimal doses, resulting in the eventual failure of therapy. This is often accompanied by the development of drug resistance and metastatic disease. Targeted drug delivery towards tumor cells, on the other hand, offers the possibility of overcoming these consequences by directing and concentrating the therapeutic agent only at the desired target site, increasing therapeutic efficacy through increased tumor cell death and decreased incidence of side effects in healthy tissues (Allen, 2002).

Tumor cells require a dedicated and effective blood supply, which cannot be provided by the existing vessels in normal tissues (Folkman, 1990). Therefore, angiogenesis, a process common on wound healing, starts to develop in order to create an appropriate blood vessel network to irrigate the novel cellular mass. Since angiogenesis is controlled by pro- and anti-angiogenic factors, it appears to be a promising target in cancer therapy (Ferrara, 2005). Angiogenic vessels present distinct features at different levels, mainly on the markers expressed at the cell surface (Carmeliet, 2003). Many of these tumor vessel markers are proteins associated with tumor-induced angiogenesis and some are specific for certain tumors (Pasqualini, 2002).

Targeting therapeutic agents to the vasculature of tumors, as opposed to the tumor cells themselves, offers some additional advantages: eliminating tumor's blood supply can profoundly suppress tumor growth; blood vessels are more readily accessible to intravenously administered therapy than tumor cells, and although tumor blood vessels acquire a tumor-associated 'signature', they are composed of normal cells that do not readily acquire mutations that could further lead to drug resistance (Boehm, 1997); in addition, tumor vascular targeting avoids problems associated with intrinsic drug resistance such as those related with poor drug penetration into a tumor due to high interstitial pressure gradients within tumors (Feron, 2004). Treatment selectivity against proliferative tumor-derived endothelial cells and minimal toxicity is likely to be achieved because angiogenesis in the adult is limited to wound healing, ovulation, pregnancy and atherosclerosis (Folkman, 2007; Folkman, 2005; Hanahan, 1996).

In general terms, treatment selectivity can be achieved by designing a system where the agent is concealed, whereas the surface is decorated in a way that it has the ability to direct the system to the target site, taking advantage of one or more distinct features of the pathological site. In this regard, one of the most important strategies in molecularly guided cancer pharmacology is the development of techniques that can modify the kinetic features of drugs by encapsulating them in nanosystems, like liposomes.

The development of physically and biological stable liposomes, composed with a hydrophilic polymer, like poly(ethylene glycol), PEG, on its surface, with an average size of 100 nm and containing chemotherapeutic drugs, such as doxorubicin, was a significant achievement that, presumably, will have a great impact in the future of nanotechnology, within the field of human health. Coating the surface of liposomes with a hydrophilic polymer like PEG, strongly contributes to the formation of a hydrophilic cloud around the liposomes (Needham, 1992 #44; Woodle, 1992 #39; Hristova, 1995 #45; Hajitou, 2006 #62). Upon intravenous injection, such hydrophilic shell dramatically decreases the rate and the extent of electrostatic and hydrophobic interactions between the surface of liposomes and blood components that mediate liposomal blood clearance and/or disintegration (Lasic, 1991; Needham, 1992; Torchilin, 1994; Woodle, 1992). The ability of drug-loaded PEG-grafted liposomes to long circulate in blood, favours their accumulation in solid tumors (Wu, 1993). Such accumulation, as well as that of macromolecules or polymeric drugs is greatly enhanced in tumor tissue relative to that in healthy tissues, a phenomenon known as *Enhanced Permeability and Retention*, being generally observed in viable and rapidly growing solid tumors (Maeda, 2001). This phenomenon is supported by an extensive angiogenesis and impaired lymphatic drainage at the tumor interstitium (Maeda, 2000). Tumor vessels possess irregular cellular lining composed of disorganized, loosely connected, branched or overlapping endothelial cells, which contribute to tumor vessel leakiness (Carmeliet, 2003; Hashizume, 2000). As an example, it was previously demonstrated that PEG-grafted liposomes, following transendothelial transport through gaps between endothelial cells, presented significant extravascular accumulation in tumors (Yuan, 1994). Further improvements in the selective toxicity of anti-proliferative drugs might be achieved by coupling ligands selective for the target cell to the liposome surface. Relatively few ligand molecules per liposome (10-20) are required to selectively deliver high payloads of drugs to target cells via the mechanism of receptor-mediated internalization (Allen, 2002). Unlike other delivery systems such as drug-immunoconjugates or -immunotoxins, which deliver few molecules of drug or toxin (<10) per antibody (or immunotoxin) molecule, ligand-targeted liposomes can be exploited to deliver thousands of molecules of drug using few tens of molecules of ligands covalently coupled on the liposome surface (Sapra, 2003). Coupling a ligand to a support should be a simple, fast, efficient and reproducible method, yielding stable, non-toxic bonds. Moreover, the coupling reaction should not alter the drug loading efficiency, drug release rates, nor the biological properties of the ligands, e.g. target recognition and binding efficiency (Papahadjopoulos, 1991).

The versatility of liposomes as a delivery system allows the control of the location (spatial delivery) as well as of the rate of release (temporal delivery) of the transported agent. pH-sensitive liposomes constitute a typical example where both spatial and temporal delivery can be achieved. They are usually composed of a neutral cone-shaped lipid like dioleoylphosphatidylethanolamine (DOPE) and a weakly acidic amphiphile, such as cholesteryl hemisuccinate (CHEMS), and designed to form a stable lipid bilayer at neutral or basic pH but to rapid destabilize in an acidifying endosome (Fonseca, 2005). Since pH-sensitive liposomes can facilitate cytosolic release of membrane impermeable molecules, it might be feasible to combine their use with a targeting ligand that promotes receptor-mediated endocytosis. Overall, the development of a sterically stabilized pH-sensitive nanosystem covalently coupled to a targeting ligand, able to target specific cells, like tumor cells and/or endothelial cells existing in tumor blood vessels, containing a chemotherapeutic drug, such as doxorubicin, can have a major impact on the therapeutic index of the encapsulated payload, in the treatment of diseases like human breast cancer.

SUMMARY OF THE INVENTION

The present invention provides a nanosystem with a pH-sensitive lipid composition (or incorporating a pH-sensitive disrupting agent), encapsulating an agent (like a drug or a diagnostic compound), and armed on the surface with a targeting ligand. Such a system, upon systemic administration, for example, has the ability to target specific cell populations like tumor cells and/or endothelial cells existing in tumor blood vessels. Upon reaching the target cells, the nanosystem is capable of binding the target cells and is internalized through receptor-mediated endocytosis, where the acidification of the milieu triggers the destabilization of the nanosystem. Such destabilization leads to release at a high rate of the associated payload to permit efficient intracellular release and, thus, increased concentration of the transported cargo at the target site. This versatile technology allows the replacement of the lipid composition, of the encapsulated payload and of the ligand, depending on the purpose (treatment or diagnostic) and/or the type of disease.

Overall, this invention provides, as a major benefit, improved therapeutic or diagnostic activity through specificity of action and triggered release of the encapsulated payload (at the level of the target cell(s)), as well as reduced adverse side-effects. The field of application includes therapy or diagnostic for cancer and for other diseases including, but not limited to inflammation, infectious diseases or eye-diseases and disorders.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
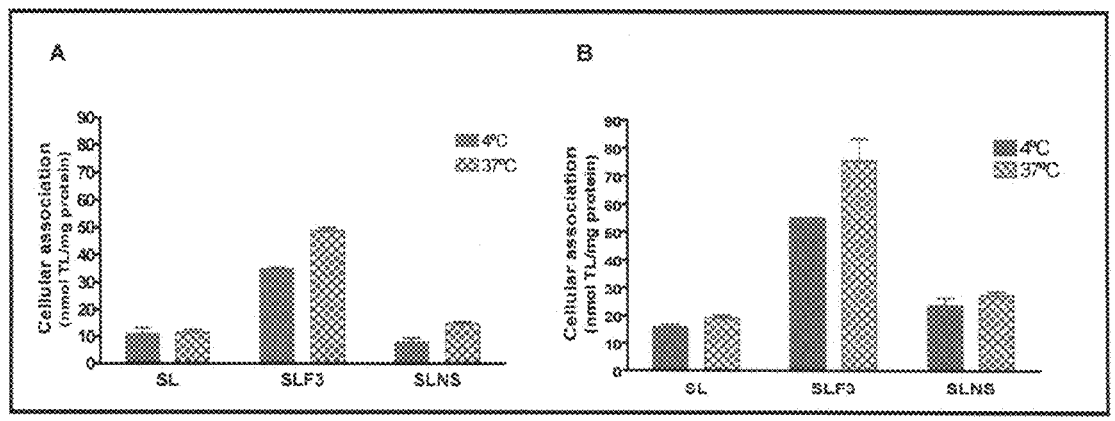
FIG. 1—Cellular association of several formulations of liposomes with human breast cancer cells or human microvascular endothelial cells. Rhodamine-labelled non-targeted (SL), F3-targeted (SLF3), or liposomes targeted with a non-specific peptide (SLNS), at 1.2 mM total lipid/well, were incubated with $10^6$ of (A) human tumor breast (MDA-MB-435S) or (B) human microvascular endothelial (HMEC-1) cell lines, at 4° C. or 37° C. for 1 h. Data are expressed as nmol of total lipid/mg protein, and are the mean of four experiments, each done in triplicate.

The present invention provides a nanosystem combining a targeting ability to specific cell subsets (like tumor cells and/or vascular cells), achieved by coupling an internalizing targeting ligand at the nanosystem surface, and triggered intracellular release (upon activation by acidification of the milieu) of the encapsulate payload at a high rate.

As shown herein, the term "payload" or "agent" means the portion of a greater whole which is distinct from the packaging required to transport it.

The term "ligand" designates the molecule linked to a support that is capable of specifically directing a system to a target. The target ligand of the invention can be an aptamer, an antibody or a fragment thereof (anti-CD19 that targets CD19 on lymphoma and multiple myeloma cells (Sapra, 2003), anti-CD31 or PECAM-1 which recognises the human CD31 cell surface antigen, anti-HER2-Fab' which binds to HER2, bevacizumab that targets the vascular endothelial growth factor (VEGF), cetuximab used against epidermal growth factor receptor (EGFR)), a protein (transferrin) a peptide (antagonist G that targets vasopressin, RGD4C for $\alpha v$ integrins, CPRECES for aminopeptidase A, CNGRC for CD13, CKGGRAKDC that homes to white fat vasculature by targeting prohibitin, KDEPQRRSARLSAKPAPPKPEPKPKKAPAKK (SEQ ID NO:1) (F3), that binds to nucleolin (Hajitou, 2006)). The term "peptide" is used broadly to designate peptides, fragments of proteins and the like, while "peptidomimetic" is used to mean a peptide-like molecule that has the binding activity of the homing peptide, including compounds that contain chemical modifications, non-naturally occurring aminoacids, peptoids and the like.

The ligand is susceptible of being identified based on its ability to home to a specific organ, like a tumor, but not to the corresponding non-target tissue. The terms "home", "selectively home" or "specific binding" mean that the targeted system interacts with the target organ, on a ligand- and on a cell-specific manner, after being administered to the subject.

As used herein, the term "tumor" includes tumor parenchymal cells, supporting stroma and angiogenic blood vessels that infiltrate the tumor cell mass. The terms "normal" or "non-tumor" are used to refer a tissue that is not a "tumor". "System" or "conjugate" refers to the combination of interdependent entities, herein presented as the agent, support and ligand, to form an integrated whole with the ability to interact with a target organ or cell.

The physical, chemical or biological material linked to a homing molecule is designated as "support" and encloses an agent to be targeted to a specific cell. Examples include liposomes, virus containing an agent such as a drug or a nucleic acid, non-toxic and biodegradable microdevices, microcapsules or a microbed composed of plastic, agarose, gelatine or other biological or inert material; a micelle, lipid micelle, nanosphere, microsphere, lipid disc. Preferably the delivery vehicle that acts as a support is a liposome composed of but not limited to fully hydrogenated soy phosphatidylcholine, methoxy-polyethylene glycol phosphatidylethanolamine, maleimide-polyethylene glycol phosphatidylethanolamine, N-methylpalmitoyloleoylphosphatidylcholine, phosphatidylserine, phosphatidylcholine, palmitoyloleoylphosphatidylcholine, dipalmitoylphosphatidylcholine, distearoylphosphatidylcholine, diphytanoylphosphatidylcholine, sphinomyelin, phosphatidylglycerol, dioleoylphosphatiylethanolamine, cholesteryl hemisuccinate, cholesterol, or a combination thereof. The support should be non-toxic to the normal expression of the cell surface molecules and to the normal physiology of the subject and must not occlude circulation. If the subject used for study is not to be sacrificed to collect a tumor or normal tissue, support should be biodegradable as well.

The term "molecule" is used herein to designate a polymeric or a non-polymeric organic chemical, a nucleic acid or an oligonucleotide, a peptide or a peptidomimetic or a protein, antibody, growth fragment or a fragment thereof presenting a linear or cyclic conformation, or a non-naturally occurring compound.

The invention provides a system composed of a support enclosing an agent, linked to a ligand that enables the selective and specific targeting towards overexpressed molecules on the target cell, in order to diagnose, treat or correct a disease and/or a disorder.

The ligand of the invention is linked to the surface of the support in a way that the specific sequence is able to interact with the target molecule overexpressed on the surface of a specific cell. An appropriate spacer, with or without a reactive group, can be positioned between the ligand and the support, in such a way that the mentioned interaction is not hindered. Conjugation of PEG to the peptide requires a suitable functional group at the end of the PEG and the N-terminal of the peptide. When an amine (-peptide-NH-PEG) is the linkage functional group, a PEG with an end-group functionalized by a halide (e.g. —Cl, —Br, and —I) or a sulfonate (e.g. —$OSO_2C_6H_4CH_3$, —$OSO_2CH_2CF_3$) can be used to couple with the amino group at the N-terminal. When a urethane (peptide-NHC(O)O-PEG) is the linkage functional group, a PEG with an end-group functionalized by an active carbonate (e.g. —C(O)-Im, —OC(O)-pNP, —OC(O)—NHS, —OC(O)-TCP) can be used to couple with the amino group at the N-terminal. When an amide (peptide-NHC(O)-PEG) is the linkage functional group, a PEG with the end-group functionalized by the activated carboxyl group (e.g., the carboxyl group activated by DCC/HOBt, DCC/dimethylaminopyridine (DMAP), DIPCDI/HOBt, and EDC/NHS) can be used to couple with the amino group at the N-terminal. When a thio ester (peptide-C(O)CH$_2$SC(O)-PEG) is the linkage functional group, a PEG with the end-group functionalized by the thio acid (-PEG-C(O)S) can be used to couple with the N-terminal modified to bromoacetyl (peptide-C(O)CH$_2$Br). When a thio ether (peptide-C(O)CH$_2$SCH$_2$-PEG) is the linkage functional group, a PEG with the end-group functionalized by the thiol group (-PEG-CH$_2$SH) can be used to couple with the N-terminal modified to bromoacetyl (peptide-C(O)CH$_2$Br). When the thioether of a maleimide/thio conjugate is the linkage functional group, a PEG with the end-group functionalized by a thiol group (C(O)-PEG-C(O)CH$_2$CH$_2$SH) can be used to couple with the N-terminal modified to the maleimide group (maleimide-CH$_2$CH$_2$C(O)-peptide) (Zalipsky, 1995).

Primary amines, present at the N-terminal of a biomolecule, can be modified with the introduction of SH groups. In a preferred embodiment of the present invention, this modification can be achieved using Traut's reagent (2-Iminothiolane hydrochloride). Thiol groups are able to react directly with maleimide present on the support surface leading to a stable thioether bond. Under these circumstances, immobilization of a thiolated peptide creates a spacer of five atoms length (maleimide-S—CH$_2$CH$_2$C(O)NH-peptide).

The reactive group present in the spacer not only can be an efficient means of linking the ligand to the support, but also can contain a tag to facilitate recovery or identification of the system. Identification of the ligand or the support linked to the ligand with a known label, allows in vitro cells or in vivo organs or tissues to be collected, molecules recovered and compared with the control cell population, organ or tissue. The term "control cell, organ or tissue" means a cell, organ or tissue other than the one for which the identification of the homing molecule is desired.

The conjugate can be multivalent, presenting more than one homing ligand that selectively homes to the designated molecule(s) on the target cells. The conjugate can be directed to the target cell by an external ligand covalently linked to its surface directly or through a reactive group inserted in the support. The homing molecule of the invention can be linked to other supports besides liposomes, such as a physical, chemical or biological delivery systems or a cell, upon administration. Also, according to the method of the invention, a variety of therapeutic agents can be directed to tumor blood vessels and tumor cells in a subject.

Doxorubicin (DXR) is a chemotherapeutic agent widely used in cancer therapy with anti-angiogenic properties (Devy, 2004). Other chemotherapeutic agents successfully used include alkylating drugs, such as cyclophosphamide, chlorambucil, melphalan, busulfan, lomustine, carmustine, chlormethine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and mitomycin; antimetabolites, such as methotrexate, capecitabine, cytarabine, fludarabine, cladribine, gemcitabine, fluorouracil, raltitrexed (tomudex), mercaptopurine, tegafur and tioguaninc; vinca alkaloids, such as vinblastine, vincristine, vindesine, vinorelbine and etoposide; other neoplastic drugs, such as amsacrine, altetarmine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane; taxanes including: docetaxel and paclitaxel; topoisomerase I inhibitors including inotecan and topotecan, trastuzumab, and tretinoin; SN-38, ET-743, TLK 286; anti-inflammatory agents: ibuprofen, aceclofenac, acemetacin, azapropazone, celecoxib, dexketoprofen, diclofenac sodium, diflunisal, cetodolac, fenbufen, fenoprofen, flubiprofen, indomethacin, acetaminocin, piroxicam, rofecoxib, sulindac, tenoxicam, tiaprofenuic acid, aspirin and benorilate; antiangiogenic agents or angiolytic agents such as but not limited to: Angiostatin (plasminogen fragment), antiangiogenic antithrombin III, Angiozyme, ABT-627, Bay 12-9566, Benefin, Bevacizumab, BMS-275291, cartilage-derived inhibitor (CDI), CAI, CD59 complement fragment, CEP-7055, Col 3, Combretastatin A-4, Endostatin (collagenXVIII fragment), Fibronectin fragment, Gro-beta, Halofuginone, Heparinases, Heparin hexasaccharide fragment, HMV833, Human chorionicgonadotropin (hCG), IM-862, Interferonalpha/beta/gamma, Interferon inducible protein (IP-10), Interleukin-12, Kringle 5 (plasminogen fragment), Marimastat, Metalloproteinase inhibitors (TIMPs), 2-Methoxyestradiol, MMI 270 (CGS 27023A), MoAbIMC-1C11, Neovastat, NM-3, Panzem, PI-88, Placental ribonuclease inhibitor, Plasminogen activator inhibitor, Platelet factor-4 (PF4), Prinomastat, Prolactin16kD fragment, Proliferin-related protein (PRP), PTK 787/ZK 222594, Retinoids, Solimastat, Squalamine, SS 3304, SU 5416, SU6668, SU11248, Tetrahydrocortisol-S, Tetrathiomolybdate, Thalidomide, Thrombospondin-1 (TSP-1), TNP-470, Transforming growth factor-beta (TGF-b), Vasculostatin, Vasostatin (calreticulin fragment), ZD6126, ZD 6474, Farnesyl transferase inhibitors (FTI), Biphosphonates. Porphyrins are also widely used in cancer treatment, as well as in the treatment of ocular diseases and disorders, within photodynamic therapy. Thus, the targeted drug can be a cytotoxic, an anti-cancer, an anti-inflammatory, an anti-angiogenic, an angiolytic, a vascular disrupting agent or an agent for photodynamic therapy. The drug or a combination of two or more drugs can be encapsulated, entrapped, intercalated within the core or associated with the delivery vehicle.

The conjugate should have a diameter comprised between 100 and 200 nm to better achieve the final purpose of encountering the target cell through the circulation by passing relatively unhindered through the capillary beds without occluding circulation (Drummond, 1999). The system is administered to the subject, which can be a vertebrate, such as a mammal, particularly a human, and passes through the tumor and its vasculature where it specifically interacts with the target cells.

Targeting selectivity depends on the overexpression of a cell surface receptor on only one or a few cell types. Controls can be a similar peptide lacking the binding sequence or a different cell line not overexpressing the receptor to the target ligand presented in example II.

A conjugate to selectively bind the target cell must overcome obstacles such as long diffusion distances, tight cell adherence, a dense fibrous stroma and the high interstitial pressure gradient towards the interior of the tumor mass (Mc-Donald, 2002). These are the reasons why vascular targeting also emerges as an agreeable option, since endothelial cells are easily accessible to a circulating conjugate. Moreover, angiogenic vessels present distinct features at different levels, such as structurally irregular walls, typically poor and abnormal blood flow and leakiness (Carmeliet, 2003; Pasqualini, 2002). Overall, these features can facilitate, on one hand, tumor metastization and, on the other hand, the therapeutic agent to reach the tumor. By affecting the ability of a tumor vascular network to organize, additional gains are expected, for example, and in the case of anticancer therapy, on the primary tumor and also on metastases. Moreover, cellular receptors express a conservative nature, which means that tumor and vascular cells, namely endothelial cells, can share the same surface markers. Thus, a tumor homing molecule that binds a target molecule in the tumor vasculature of a mouse is also capable of binding to the corresponding target molecule in the tumor vasculature of a human or other mammalian. In fact, the same target molecule can be shared by different tumors (Folkman, 1997). However, for the final purpose of administering a therapeutic conjugate to a subject, such as a mammal, one must possess pharmaceutical acceptable properties according to the route of administration and target location. Several systems, like liposomes, are non-toxic, biocompatible, easily made and administered, which are advantageous characteristics for parenteral administration in an effective amount to permit therapeutic, diagnostic or detecting effect.

The term "effective amount" refers to the necessary quantity for producing the desired action.

The conjugate can incorporate a chemotherapeutic or cytotoxic agent, a diagnostic agent, a detecting agent or a gene therapeutic agent. The content of the conjugate can be incorporated or encapsulated in a passive or active manner and the delivery mechanism can be controlled by engineering the system composition. The tumor microenvironment exhibits unique features that can be advantageous to promote disruption of the system and its content release. Poor vascular organization and impaired lymphatic drainage lead to the accumulation of products of cellular metabolism, such as lactic and carbonic acid, which lowers the extracellular milieu pH value (Gatenby, 2004). The same happens in the endosomal pathway, where disruption and content release of the conjugate take place in early and late endosomes (Simoes, 2004).

Liposomes can be composed of weakly acidic amphiphiles and neutral cone-shaped lipids to allow control over the disruption of the lipid membrane. At physiological pH, stable liposomes are formed, but acidification triggers protonation of the carboxylic groups of the amphiphiles, such as CHEMS (Straubinger, 1993), reducing their stabilizing effect and thus leading to liposomal destabilization, since under these conditions, cone-shaped molecules like phosphatidylethanolamine (PE) revert into their inverted hexagonal phase. The choice of the amphiphilic stabilizers as well as its molar percentage with respect to the PE content are imposed by the desired properties of the liposomes, including the extent of cellular internalization, the fusogenic ability, pH-sensitivity and stability in biological fluids (Drummond, 2000).

A more rapid rate of drug release from endosomes or lysosomes, leads to more rapid delivery of the drug to its intracellular site of action, resulting in improved therapeutic efficacy (Ishida, 2006).

In the example illustrated herein, the receptor that specifically binds the tested ligand has been identified as nucleolin (Christian, 2003).

Nucleolin is a ubiquitous, nonhistone nucleolar phosphoprotein of exponentially growing eukaryotic cells. It is described as having a role in controlling the organization of nucleolar chromatin, packaging of pre-RNA, rDNA transcription and ribosome assembly. Therefore, it is implicated in proliferation and growth, cytokinesis, replication, embryogenesis and nucleogenesis. The protein appears in cells before transcription and ribosome synthesis starts (Srivastava, 1999).

The nucleolin polypeptide consists of a negatively charged $NH_2$-terminal domain, an RNA-binding domain and a COOH-terminal domain rich in RGG motifs. The first region has an analogous high-mobility group function. Phosphorilation of this domain enhances nucleolin degradation by proteases, compromising its stability, but it is crucial for rDNA transcription. The central globular domain is involved in pre-RNA recognition, condensing and packaging in the nucleolus. The carboxyl-terminal domain controls nucleolin interaction with ribosomal proteins by permitting RNAs access to the RNA binding motifs located in the central region of nucleolin. Both amino and carboxyl terminals can be regulated by proteolysis. Cleaved nucleolin activates autolytic endonucleases, which fragment DNA to cause apoptosis. In proliferating cells, the expression of a proteolytic inhibitor prevents nucleolin's self-degradation. Therefore, the levels of this protein are elevated in tumor and other rapidly dividing cells (Srivastava, 1999).

A homing molecule for nucleolin can be an anti-nucleolin antibody or a high mobility group protein (HMGN-2) derived peptide, such as the 31-amino acid fragment that corresponds to the sequence KDEPQRRSARLSAKPAPPKPEPKPKKA-PAKK (SEQ ID NO:1) (F3), identified by phage display libraries (Porkka, 2002). F3 binds to the $NH_2$-terminal domain of nucleolin and can accumulate preferentially in angiogenic vasculature of tumors as compared to non-tumor vessels. Since nucleolin is present in the cell surface in a phosphorilated form and in the nucleus membrane, the peptide can be internalized by its specific target cells and be transported to the nucleus. It is recognized that the F3 peptide shown herein is useful for tumor and endothelial cell homing (Porkka, 2002) and that it can be attached to a support to form a conjugate that can carry a payload such as a chemotherapeutic agent, a diagnostic agent or an imaging agent directed to cells involved in tumor growth.

As shown in Example 1, for active encapsulation of the lipid-based system covalently coupled with the F3 peptide, the mixture of liposome-forming lipids is dried to form a thin film and hydrated with an aqueous medium containing the solute species that will form the aqueous phase in the interior of the vesicle. Afterwards, those species are removed and the drug is added to the exterior of the liposome for remote loading. Methods such as size exclusion chromatography, dialysis or centrifugation can be applied to remove the non-encapsulated drug. In another embodiment, a trapping agent can be included in the interior of the liposome to complex with the encapsulating agent and lead to its retention.

The use of lipids with high transition temperatures (distearoylphosphatidylcholine (DSPC); hydrogenated soy phosphatidylcholine (HSPC)) and the incorporation of cholesterol (CHOL) and lipid conjugates such as distearoylphosphatidylethanolamine polyethylene glycol (DSPE-PEG), lead to a significant decrease of leakage of the encapsulated drugs during blood circulation or in the extracellular milieu. Moreover, such lipids also reduce non-specific interactions between the liposomes and serum proteins (opsonins), thus preventing liposome clearance by the cells of the reticuloendothelial system (RES), increasing circulation time for optimizing the interaction of the system with the target cells (Allen, 1987; Gabizon, 1992).

Size of liposomes can be engineered by forcing the passage of the vesicles through appropriate pore size membranes in an extruder. It is advised for liposomes to have a size small enough to allow its passage through capillaries and to extravasate from the vascular compartment if tumor cells are to be targeted (Yuan, 1994).

F3, used as an example in this description, is coupled to the surface of the liposome by an imidoesther link between the thiol group of the derivatized peptide and the maleimide group on the surface of the support. Conjugating a peptide to a support can potentially affect the system's homing capacity. As shown herein, peptide specificity and ability to home to the target receptor are not affected (Examples II and III). It is important to emphasize that the encapsulation of an agent is also susceptible to compromise its desired action. In the present case, it is demonstrated that the encapsulated agent maintains its characteristic features and action (Examples II and III).

Cellular internalization studies were performed by comparison of cells incubated with target or non-targeted conjugates at internalization permissive (37° C.) and non-permissive (4° C.) temperatures. Results confirm the importance of the ligand in the recognition of the system by the target cells. Moreover, other cell lines, such as MCF-7 and TSA show no difference between the internalization levels of the targeted and non-targeted conjugate, which indicates that the system is capable of homing to a specific tumor and tumor vascular endothelial cells. Specificity of the targeting ligand is confirmed by a competitive binding assay (Example II).

The mechanisms by which a system enters into a cell are distinct and usually divided into two broad categories: phagocytosis, a process restricted to specialized mammalian cells, and pinocytosis, which occurs in all mammalian cells and comprehends macropinocytosis, clathrin-mediated endocytosis, caveolae-mediated endocytosis, as well as other less characterized clathrin- and caveolae-independent endocytic pathways (Conner, 2003).

As shown in Example III, internalization into the cells is strongly energy-dependent and the clathrin-mediated endocytotic pathway appears to be the most probable portal of entry of the conjugate into tumor and endothelial cells of angiogenic blood vessels.

Confocal microscopy observations corroborate the results from internalization studies (Example II). Non-targeted controls show no staining for the lipid marker as opposed to the F3-targeted samples. Cells incubated with ligand targeted pH-sensitive liposomes show a more evident green intracellular staining than targeted non-pH-sensitive liposomes. Such results indicate that therapeutic gains can be expected with a targeted formulation capable of promoting intracellular triggered release of an encapsulated agent to both tumor and endothelial cells in a subject.

The antitumor and the anti-angiogenic activity of doxorubicin make it a good model to demonstrate the potential of the invented technological platform. As an example, doxorubicin is encapsulated in a lipid-based nanosystem, covalently coupled to a peptide, and incubated with breast cancer and endothelial cells in different ranges of drug concentration during predetermined times (Example IV).

Results demonstrate that the cytotoxic activity of the drug delivered by the targeted system of the invention is increased against nucleolin-overexpressing cells as compared to nucleolin non-overexpressing cells. Incubation of cells with a system composed of a therapeutic agent and a target homing molecule is more effective in causing cell death than incubation with the system without the specific ligand. Cytotoxicity of doxorubicin-containing peptide-targeted lipid conjugates against MDA-MB-435S (breast ductal carcinoma cells) and HMEC-1 (human mammary epithelial cells) was compared in vitro to free doxorubicin, doxorubicin-containing non-targeted conjugates or conjugates targeted by a non-specific peptide. Results demonstrate that selective accumulation of the conjugate increases toxicity of the agent, reducing the dosage required for inducing 50% of cell death.

The system's unique composition allows specific interaction with target cells along with programmed intracellular delivery of the payload, resulting in higher efficiency of action of the transported agent. These features are congregated for the first time on the same technological platform, differentiating it from those reported in the literature.

Documents WO 2005/094383, WO 2000/023570, WO 2007/039783, WO 2003/084508, WO 2001/085093 and WO 1998/016201 refer to lipid-based nanovesicles with the ability to promote triggered release, upon an adequate stimulus. Nevertheless, the system described herein is unique in terms of its lipid composition and targeting specificity, mechanism of payload release and has the additional advantage of exhibiting adequate properties for intravenous administration such as: prolonged blood circulation times due to reduced non-specific interactions with serum proteins (opsonins), thus preventing liposome clearance by the cells of the reticuloendothelial system (RES); a diameter small enough to avoid emboli or stroke, upon administration, and to facilitate extravasation from blood vessels into the tumor mass.

Document WO 2003/087124, although it mentions the F3 ligand to exemplify the targeted nanosystem herein, it does not include lipid-based nanovesicles with the ability to promote intracellular triggered release of the associated payload.

Document WO 2007/100904 refers to F3 peptide as one of the putative specific ligand of a L-methionase-drug conjugate which does not have the ability to be internalized by tumor vasculature endothelial cells and is not a lipid-based system.

Document WO 2005/019429 refers to two different levels of cellular targeting: tumor and endothelial cells. However, the purpose of that invention (enhancing phagocytosis or phagocyte activity) is fairly different from the one described herein (enhance receptor-mediated endocytosis to diagnose, treat or correct a disease and/or a disorder).

The present invention satisfies the need for selectivity and programmed delivery of a payload to specific cell populations within a target organ, like for example, tumor and/or vascular cells (endothelial cells, mural cells) of tumor angiogenic blood vessels, inhibiting, in the case of a tumor, its growth, development and metastization.

EXAMPLES

The following examples are intended to illustrate but not limit the present invention.

Example I

Preparation and Characterization of Different Lipid-Based Nanosystems

This example provides methods for encapsulating a payload such as a chemotherapeutic agent into a lipid-based nanosystem and for coupling a homing molecule such as peptide to its surface.

Non-pH-sensitive liposomes were composed of fully hydrogenated soy phosphatidylcholine, cholesterol, distearoylphosphatidylethanolamine methoxy(polyethylene glycol) (2000); distearoylphosphatidylethanolamine maleimide(polyethylene glycol) (2:1:0.06:0.04, molar ratio). The lipid film was hydrated at 65° C. in 250 mM ammonium sulphate solution pH 5.5.

The pH-sensitive formulation was composed of dioleoylphosphatidylethanolamine, cholesteryl hemisuccinate, fully hydrogenated soy phosphatidylcholine, cholesterol and distearoylphosphatidylethanolamine methoxy(polyethylene glycol) (2000); distearoylphosphatidylethanolamine maleimide(polyethylene glycol) (4:2:2:2:0.18:0.12, molar ratio). The lipid film was hydrated at 65° C. in 250 mM ammonium sulphate solution pH 8.5.

Both formulations were extruded sequentially through polycarbonate membranes of 0.2 and 0.1 μm pore size at 65° C. using a LipoFast mini extruder (Lipofast, Avestin) to obtain a uniform size distribution (Daleke, 1990). The buffer was exchanged in a Sephadex G-50 column equilibrated with 100 mM $NaCH_3COOH$/70 mM NaCl pH 5.5 for the non-pH-sensitive formulation and with 25 mM Trizmabase/10% sucrose pH 9 for the pH-sensitive formulation. Doxorubicin was then incubated with liposomes for 1 h at 65° C., in the absence of light and encapsulated by the ammonium sulphate gradient method (Bolotin EM, 1994). Free doxorubicin was removed by running the liposomes through a Sephadex G-50 column equilibrated with 25 mM 4-(2-hydroxyethyl)-1-piperazineethanesulfonic acid (HEPES)/140 mM NaCl buffer pH 7.4 (HBS) (for non-targeted liposomes), 25 mM HEPES/25 mM MES (2-(N-morpholino)ethanesulfonic acid)/140 mM NaCl pH 6.5 (for targeted non-pH-sensitive liposomes) or 25 mM HEPES/25 mM MES/140 mM NaCl pH 7.2 (for targeted pH-sensitive liposomes). To further prepare targeted liposomes, the thiolated derivative of F3 peptide (Genosphere Biotechnologies) was obtained by reaction of the peptide with 2-mercaptopropionimidate hydrochloride (a.k.a. 2-iminothiolane), at a 1:5 molar ratio in 25 mM HEPES/140 mM NaCl buffer (pH=8), for 1 h at room temperature. Liposomes were then incubated overnight at room temperature with the activated peptide at a maleimide/activated peptide molar ratio of 1:2. Activation and coupling of F3 peptide took place in an inert $N_2$ atmosphere in siliconcoated glassware (Sigmacote, Sigma). Free maleimide groups were quenched by incubation with an excess of 2-mercaptoethanol for 30 min at room temperature. Uncoupled peptide was separated in a Sepharose CL-4B column equilibrated with HBS pH 7.4.

Final lipid concentrations were determined based on lipid phosphorous assay by Fiske and Subarrow (Bartlett, 1959). The encapsulated doxorubicin was quantified by measuring UV absorbance at 492 nm. A final concentration of 120-180 µg of doxorubicin per µmol of phospholipid (95% loading efficiency) was achieved. Loading efficiency was determined using the formula [(DXR final concentration/Total lipid final concentration)/(DXR initial concentration/Total lipid initial concentration)]×100. The size of the liposomes varied between 100-150 nm, measured by dynamic laser scattering with a Coulter submicron particle size analyzer.

Example II

Cellular Association Studies

Cellular Culture

MDA-MB-435S and HMEC-1 cells were cultured in RPMI 1640 (Sigma) supplemented with 10% (v/v) heat-inactivated Foetal Bovine Serum (FBS) (Invitrogen), 100 U/ml penicillin, 100 µg/ml streptomycin (Sigma) (full medium) and maintained within their exponential growth phase at 37° C. in a humidified incubator (90% humidity) containing 5% $CO_2$. HMEC-1 cells medium was also supplemented with 10 ng/ml mouse epidermal growth factor (EGF) and 1 µg/ml hydrocortisone (Sigma). MCF-7 (ATCC) and TSA (ATCC) were grown in Dulbecco's Modified Eagle's Medium (DMEM) (Sigma), supplemented as described above (full medium).

Cellular Association Studies

Cellular association studies were performed by fluorimetry, flow cytometry and confocal microscopy.

Rhodamine-labelled liposomes (targeted, targeted by a non-specific (NS) peptide—ARALPSQRSR (SEQ ID NO:2) (Porkka, 2002)—or non-targeted), were incubated with one million of tumor (MDA-MB-435S) or endothelial cells (HMEC-1) at 4 or 37° C. and within a lipid concentration range of 0.1-1.2 mM of total lipid/well.

To assess cellular association by fluorimetry, cells were lysated and rhodamine's fluorescence was measured in the supernatant in a SpectraMax Gemini EM plate reader fluorimeter (Molecular Devices). Cellular protein was determined by the BCA™ Protein Assay Kit (Pierce). Results were expressed as nmol of total lipid/mg of protein.

To determine cellular association and payload delivery by flow cytometry, cells were incubated with rhodamine-labelled or calcein loaded liposomes at 37 or 4° C., for 1 h, detached with dissociation buffer, washed with phosphate buffer saline pH=7.4 (PBS) and immediately run in a FACSscan (Becton Dickinson) for detecting cell associated rhodamine (FL2-H) and calcein (FL1-H). A total of 40,000 events were collected and files were analysed with Cell Quest Pro software.

Figure 2:
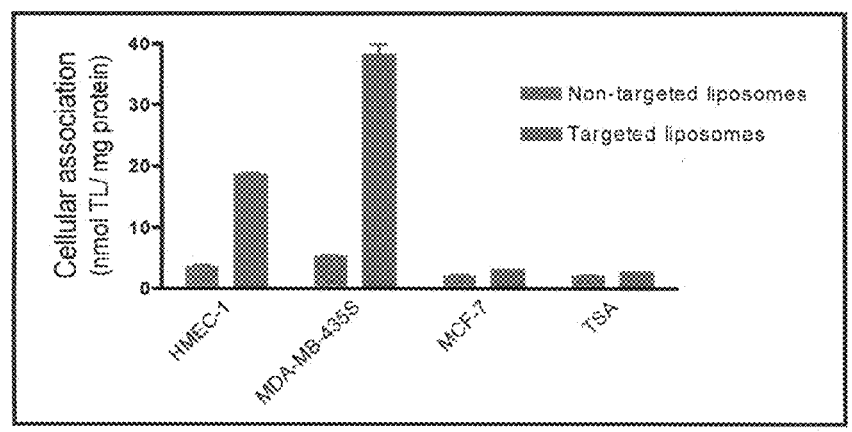
FIG. 2—Cellular association of several formulations of liposomes with specific and non-specific cell lines. Rhodamine-labelled SL or SLF3 were incubated with $10^6$ of specific (MDA-MB-435S or HMEC-1) or non-specific (MCF-7 or TSA) cell lines, for 1 h at 4° C. or 37° C. The results are shown as the mean value of triplicates from a representative experiment.

At 37° C., the extension and the rate of cellular association and delivery of the payload observed for peptide-targeted liposomes was higher than the one observed for non-targeted liposomes or liposomes targeted by a non-specific peptide, pointing out that the interaction of the former with the target cells was peptide-specific (FIG. 1). The improved cellular association revealed to increase with the increase of the lipid concentration (data not shown). The substantial increase in the levels of association for peptide-targeted liposomes as the temperature was raised from non-permissive (4° C.) to permissive temperatures (37° C.) for endocytosis, suggested that they were being internalized (FIG. 1). Targeted and non-targeted liposomes presented similar extensions of cellular uptake when incubated with non-specific cell lines like the TSA and MCF-7 cells, revealing that the interaction of F3-targeted liposomes was cell-specific (FIG. 2).

Further evidence to support the endocytosis of the targeted liposomes comes from the intracellular fluorescence observed in confocal experiments performed at 37° C. as opposed to what happened at 4° C., where little or no staining is observed.

Liposomes were double-labelled with rhodamine (red label of the lipid membrane) and calcein (green label of the aqueous core). MDA-MB-435S or HMEC-1 cells were seeded on glass cover slips in 12-well flat bottom plates at a density of $2\times10^5$ cells per well. After complete adhesion, cells were incubated at 4 or 37° C. with the fluorescently-labelled liposomes for 1 h and washed three times with PBS, following by fixation with 4% paraformaldehyde in PBS during 20 min at room temperature. After washing with PBS, cells were mounted on Moviol® mounting medium (Calbiochem) and visualized with a LSM-510 laser-scanning confocal microscope (Carl Zeiss LSM510 Meta, Zeiss), using a 488 nm and 561 nm excitation laser and a 63×/1.40 oil objective. Cells were optically sectioned and images (512×512 pixel) were acquired using the LSM-510 software. All instrumental parameters pertaining to fluorescence detection and images analyses were held constant to allow sample comparison.

Results from confocal microscopy on the intracellular uptake of F3-targeted liposomes demonstrate that after 1 h incubation, rhodamine-labelled (red) liposomes, whether pH-sensitive or non-pH-sensitive, are localized inside the target cells. In contrast, after incubation with non-targeted liposomes, no red fluorescence is observed inside or outside the cells. Cells incubated with the non-specific peptide for the target molecule overexpressed on the cell surface, exhibit only a mild red fluorescence. These findings corroborate the different levels of cellular rhodamine content quantified by fluorimetry and flow cytometry in both tumor and microvascular endothelial cells incubated with the different formulations. Moreover, a diffuse intracellular green staining is observed upon incubation with calcein loaded pH-sensitive targeted liposomes at 37° C., as opposed to the punctuated staining observed with the targeted non-pH-sensitive formulation, confirming an improved intracellular release of the liposomal payload when delivered by the former formulation.

Competitive Inhibition

Cells were plated on a 48-well flat bottom plate at a density of one million cells per well. After adherence, cells were pre-incubated 30 min with free F3 peptide at a non-toxic concentration of 50 µM at 4 or 37° C. Controls were incubated with culture medium. Afterwards, F3-targeted PEG-grafted rhodamine-labelled liposomes were added and further incubated for 1 h at the mentioned temperatures. Cellular association was assessed by fluorimetry as previously described.

Figure 3:
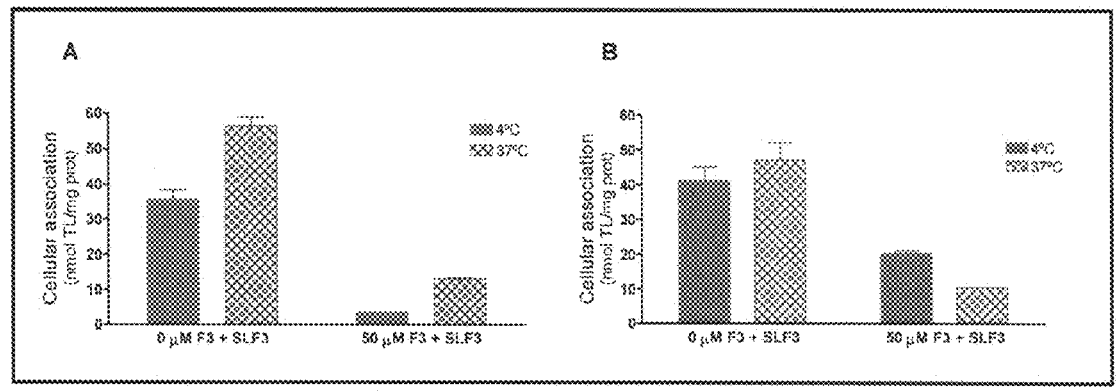
FIG. 3—Competitive inhibition assay of cellular association of SLF3 with specific cell lines. One million of (A) human tumor breast (MDA-MB-435S) or (B) human microvascular endothelial (HMEC-1) cells were pre-incubated with 50 µM of free F3 peptide or without the peptide for 30 min at 37° C., followed by 1 h incubation with rhodamine-labelled SLF3 (at 0.8 mM TL/well) at 4° C. or 37° C. The results are shown as the mean value of triplicates from a representative experiment.

The homing of the F3-targeted PEG-grafted liposomes to breast cancer cells is inhibited when synthetic F3 peptide is pre-incubated with the target cells (FIG. 3), suggesting, in agreement with the results from fluorimetry, flow cytometry and confocal experiments, that the system is being internalized by receptor-mediated endocytosis.

Example III

Mechanisms of Cellular Uptake

Macropinocytosis, a distinct form of endocytosis, depends on a sodium gradient and can be blocked by amiloride and N-ethyl-N-isopropylamiloride (EIPA), inhibitors of a $Na^+/H^+$ exchanger. It also depends on F-actin microfilament rearrangement and on phosphoinositide 3-kinase (PI3), a key enzyme in the downstream signaling of macropinocytosis. The inhibition of F-actin elongation by cytochalasin B and of PI3 by wortmannin and LY-294002 blocks macropinocytosis efficiently (Rejman, 2005). Dextran labelled with FITC (FITC-Dextran, Sigma), used as a control for this pathway, was incubated with cells to evaluate the efficiency of the inhibition by wortmannin and LY-294002.

MDA-MB-435S and HMEC-1 cells were seeded on 48-well plates at a density of one million cells per well and allowed to adhere for 24 h. Afterwards, they were pre-incubated with the inhibitors for 30 min and subsequently co-incubated with rhodamine-labelled SLF3 for 1 h. The cellular content of rhodamine of the inhibitor-treated groups was then compared with an inhibitor-free control. Results were calculated according to the formula: (concentration of the label in inhibitor-treated cells/concentration of the label in inhibitor-free cells)×100.

Figure 4B:
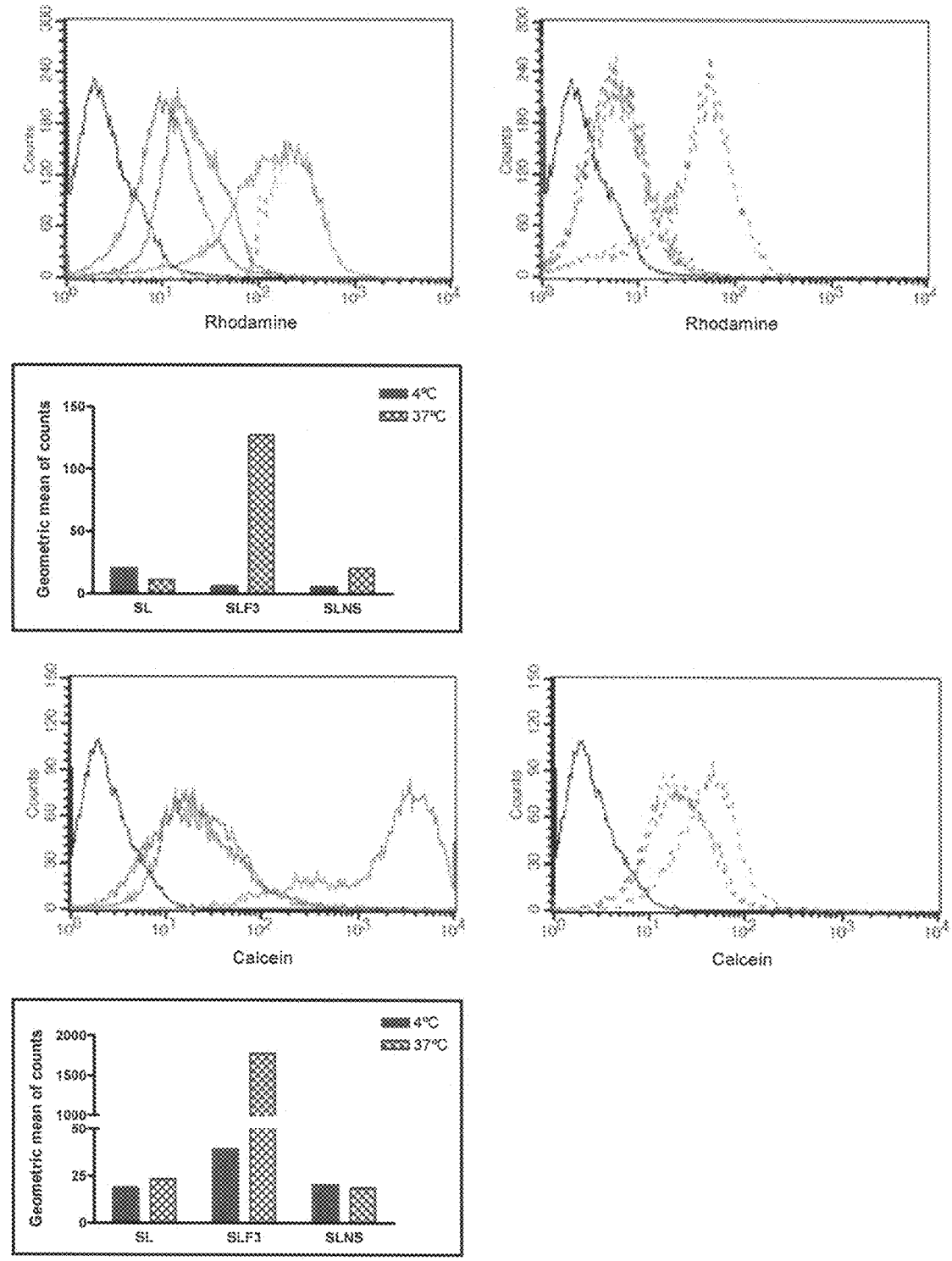
FIG. 4—Cellular association of several formulations of liposomes with human breast cancer cells or human microvascular endothelial cells analysed by flow cytometry. One million of (A) human tumor breast (MDA-MB-435S) or (B) human microvascular endothelial (HMEC-1) cells were incubated with SL (green), SLF3 (pink), or SLNS (blue) liposomes labelled with rhodamine or encapsulating calcein at a concentration of 0.6 mM TL/well, for 1 h at 4° C. (dotted line) or 37° C. (solid line). Cells were detached with dissociation buffer, washed with phosphate buffer saline pH=7.4 (PBS) and immediately run in a FACSscan (Becton Dickinson) for detecting cell associated rhodamine or calcein. The difference between cellular association of SLF3 rhodamine-labelled liposomes at 37° C. and 4° C. is represented by a dotted purple line.
Figure 5:
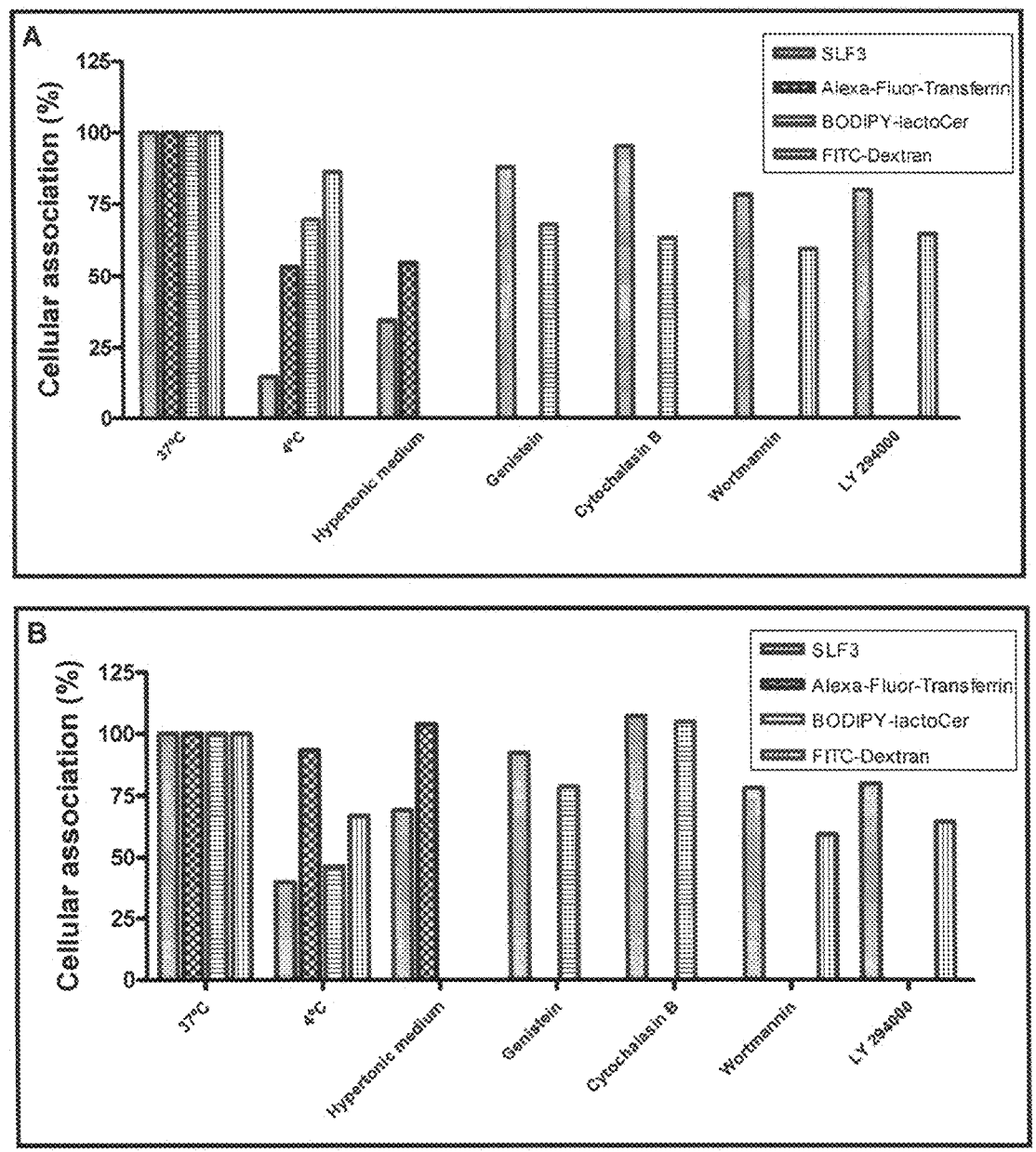
FIG. 5—Effect of several endocytosis inhibitors on the cellular association of SLF3 with (A) MDA-MB-453S or (B) HMEC-1 cells. One million of (A) human tumor breast (MDA-MB-435S) or (B) human microvascular endothelial (HMEC-1) cells were pre-incubated with 0.45 M sucrose medium, 200 µM genistein and 0.03 µM wortmannin and 50 µM LY-29400 for 30 min at 37° C., for the purpose of inhibiting clathrin- and caveolae-mediated endocytic pathways and macropinocytosis, respectively. Afterwards, cells were incubated with rhodamine-labelled SLF3 (0.2 mM TL/well for 1 h) or with the corresponding control of each pathway: Alexa-Fluor-Transferrin (0.05 mg/ml for 30 min), BODIPY®-LactoCer (0.5 mM for 10 min) or FITC-Dextran (10 mg/ml for 1 h) to evaluate the efficacy of the inhibition of clathrin- and caveolae-mediated endocytic pathways and macropinocytosis, respectively. Cellular association of each control and rhodamine-labelled SLF3 was also performed at 4° C. without pre-treatment with inhibitors. Data are shown as means±S.D., based on triplicates of at least two independent experiments.
Figure 6A:
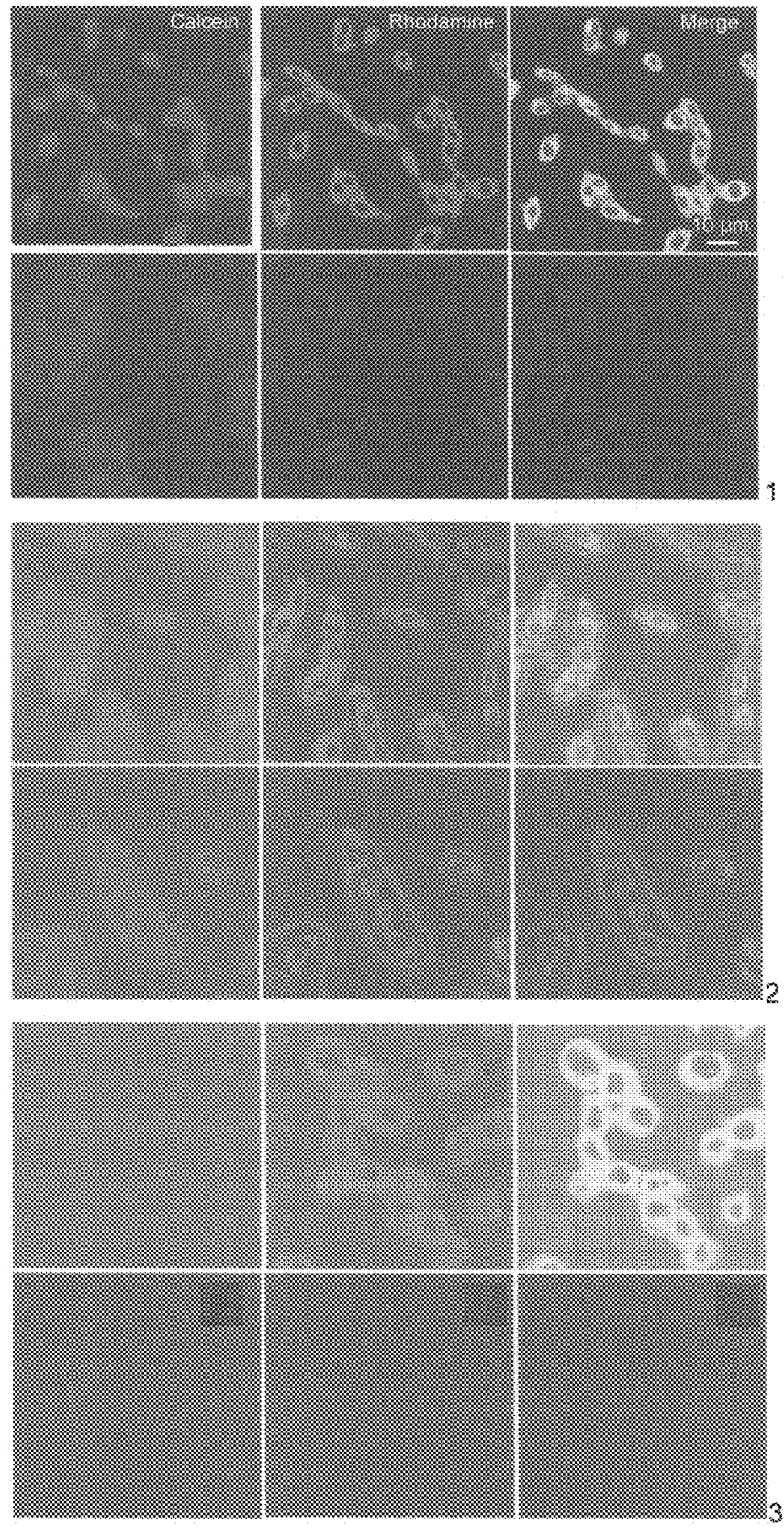
FIG. 6—Cellular association of several formulations of liposomes with human breast cancer cells or human microvascular endothelial cells analysed by confocal microscopy. (A) Human tumor breast (MDA-MB-435S) or (B) human microvascular endothelial (HMEC-1) cells were incubated with non-pH-sensitive (1) SLF3, (2) SL, (3) SLNS or with pH-sensitive (4) SLF3, (5) SL, (6) SLNS liposomes labelled with rhodamine and encapsulating calcein at a concentration of 0.6 mM TL/well, for 1 h at 37° C. (upper row) or 4° C. (lower row). Cells were washed with PBS, fixed in 4% paraformaldehyde, mounted on Moviol® mounting medium (Calbiochem) and visualized with a LSM-510 laser-scanning confocal microscope (Carl Zeiss LSM510 Meta, Zeiss). All instrumental parameters pertaining to fuorescence detection and images analyses were held constant to allow sample comparison.
Figure 6A:
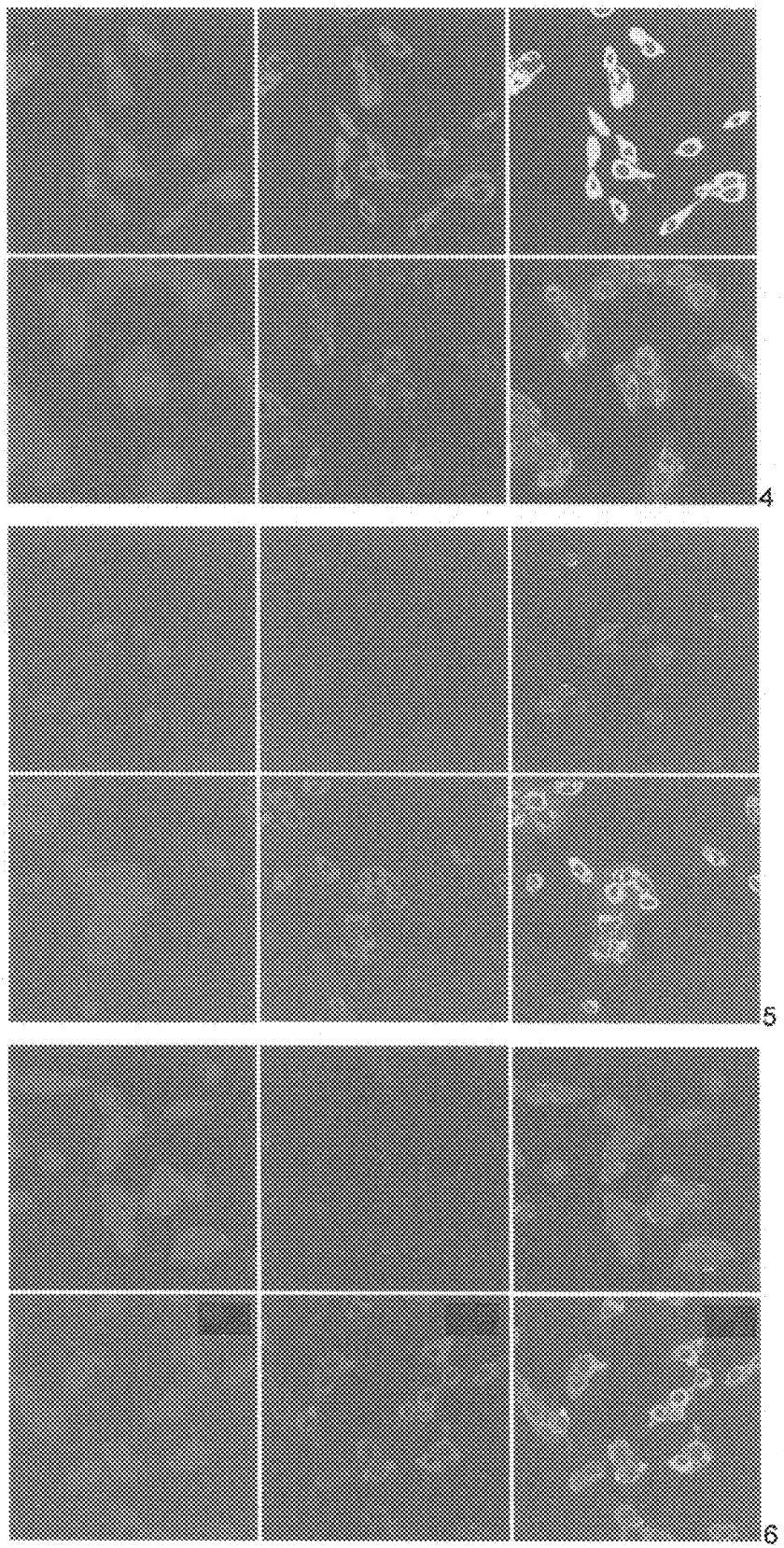
Figure 6B:
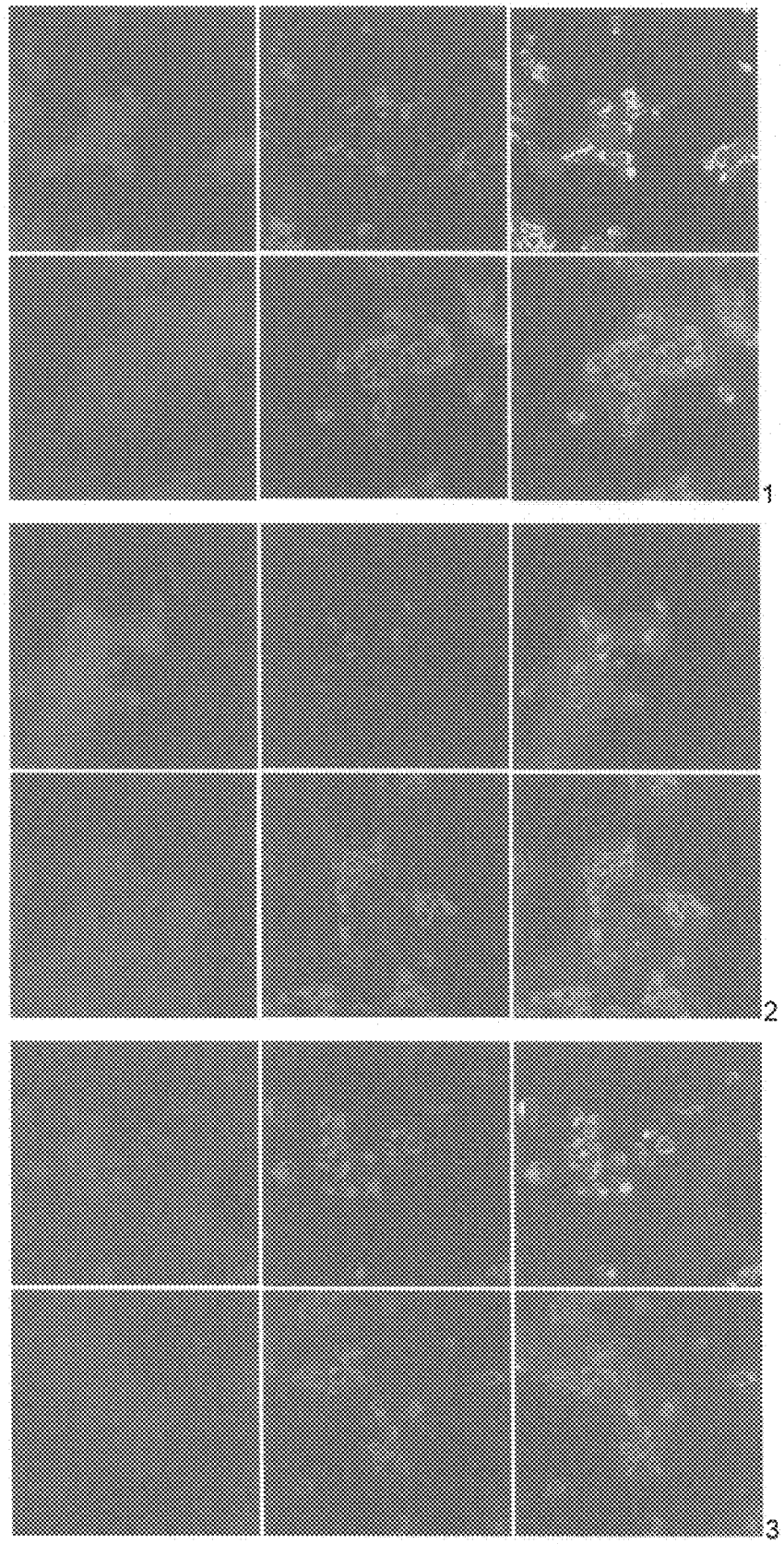
Figure 6B:
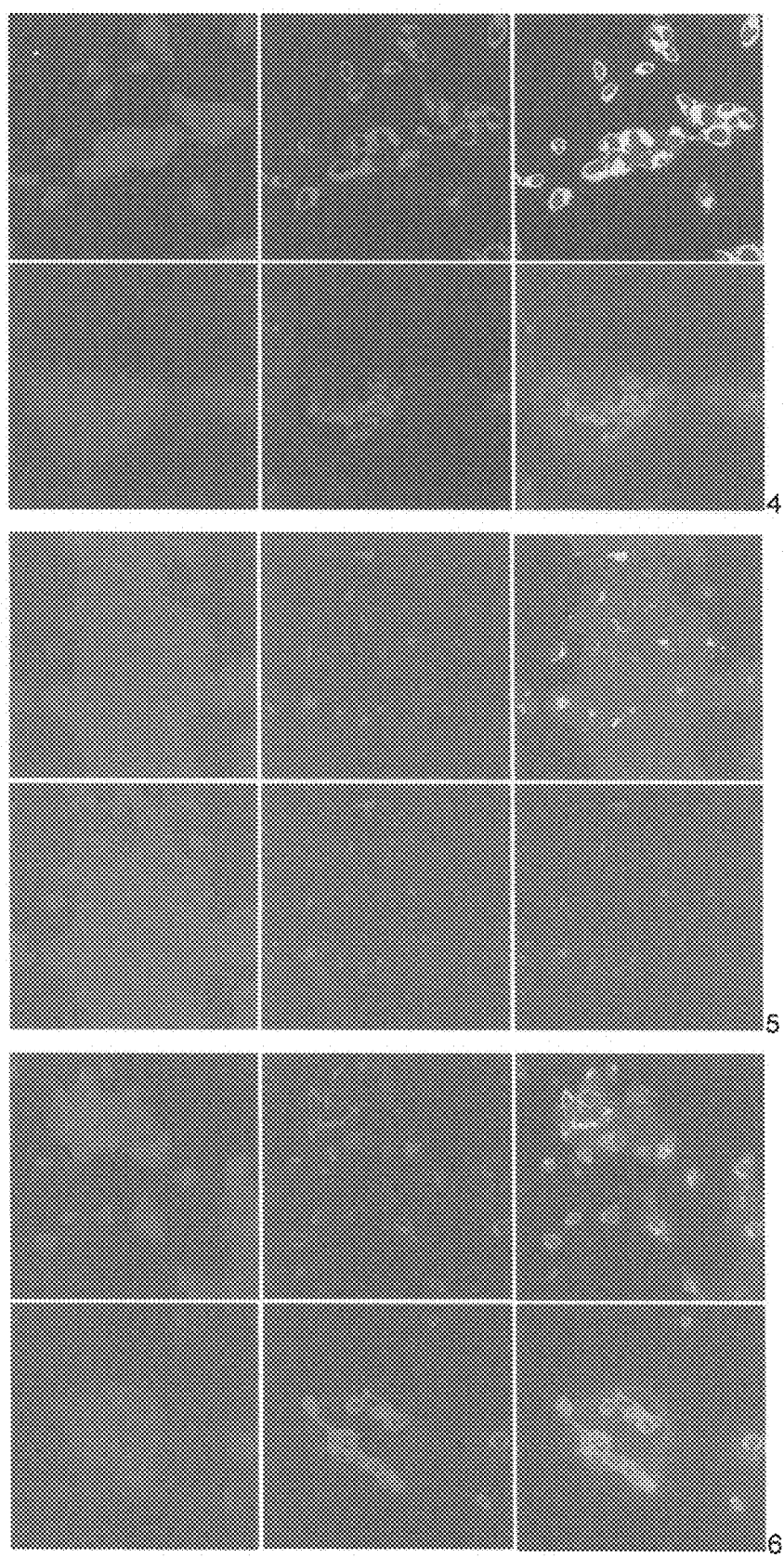

As depicted in FIGS. 4 and 5, cytochalasin B does not decrease cellular content of rhodamine, whereas wortmannin and LY 294002 inhibition cause a minor decrease of approximately 20% in both cell lines. This demonstrates that macropinocytosis is not a major pathway regarding the intracellular accumulation of F3-targeted liposomes.

Caveolae-mediated endocytosis is another portal of entry into the cell and is known to be inhibited by filipin and genistein (Rejman, 2005). BODIPY-lactosylceramide (BODIPY-lactocer, Molecular Probes) reported to be exclusively internalized via caveolae-mediated mechanism (Puri, 2001), was used as a control for the inhibition of this pathway. Genistein-mediated blockade of tyrosine kinases necessary for this type of endocytosis results in a slight decrease in the cellular content of rhodamine (12.2% of control for MDA-MB-435S and 7.87% for HMEC-1 cells).

In further experiments, clathrin-mediated endocytosis was blocked with hypertonic medium. Alexa-Fluor-Transferrin (Molecular Probes) was used as the positive control to assess the efficiency of the previous-mentioned inhibitors. A strong decrease of cellular content of rhodamine (65.7% in MDA-MB-435S cells and 31% in HMEC-1 cells) is observed after treatment with 0.45 M sucrose. These results corroborate the observation previously-mentioned in example II that internalization into the cells is strongly energy dependent, since a decrease in the incubation temperature from 37 to 4° C. was accompanied by a 2.4-fold lowering of the cellular content of rhodamine. Furthermore, these studies indicate that F3 peptide-targeted liposomes are internalized by a receptor-mediated mechanism, most likely through the clathrin-mediated endocytosis pathway, which is reinforced by the results from competitive inhibition described in example II, where cells previously incubated with the free peptide exhibited a decrease in the content of rhodamine as opposed to control cells not incubated with the peptide.

Example IV

Cytotoxicity Studies

In vitro cytotoxicity of free doxorubicin (DXR) and DXR-containing liposomes was determined for MDA-MB435S and HMEC-1 cells using the MTT (3-(4,5-Dimethylthiazol-2-yl)-2,5-diphenyltetrazolium bromide) proliferation assay (Mosmann, 1983). Briefly, cells were plated in 96-well plates at a density of 8,000 cells per well and incubated with free DXR, non-targeted pH-sensitive (or non-pH-sensitve) liposomes containing DXR or targeted pH-sensitive (or non-pH-sensitive) liposomes containing DXR. Additional controls included free peptide and empty targeted liposomes. Cells were incubated for 1, 3, 24 and 48 h at 37° C. in an atmosphere of 95% humidity and 5% $CO_2$. At the end of the incubation time, cells were gently washed twice with cold PBS to remove DXR and maintained in fresh medium for a total of 96 h. After incubation, the medium was replaced by a solution of 0.5 mg/ml MTT and the cells were further incubated for 4 h at 37° C. in an atmosphere of 95% humidity and 5% $CO_2$. Crystals were dissolved in acidic isopropanol and absorbance in each well was read at 570 nm in a microplate reader (Multiscan EX—Thermo Electron Corporation). $IC_{50}$ of DXR mediated by the different formulations was determined from the dose/response curves.

The cytotoxicity of DXR, either free or encapsulated in PEG-grafted liposomes, was compared as a function of time. $IC_{50}$ decreases as the exposure of cells to drug increases from 1 h to 48 h (Table 1). After 24 h of incubation, SLF3[DXR] is at least 17-fold more cytotoxic than SL[DXR] against MDA-MB-435S cells and 4.4-fold more cytotoxic against HMEC-1 cells, suggesting that binding and internalization of the targeted liposomes are contributing to the increased cytotoxicity. This observation is reinforced by the non-cytotoxic nature of the empty liposomes and by the fact that all of the lipid-based formulations tested showed minimal leakage in HBS and culture medium (data not shown). As demonstrated by confocal microscopy, the pH-sensitive formulation allows a large amount of drug to become rapidly bioavailable, leading to an increased intracellular concentration of DXR, which justifies the higher levels of cytotoxicity.

Free DXR has the highest levels of cytotoxicity against all the cell lines in vitro, but it does not distinguish between target receptor-expressing and target receptor-nonexpressing cell lines. It is important to point out that the in vitro cytotoxicity results obtained with free drug do not take into account the unfavourable pharmacokinetics and biodistribution that doxorubicin presents in vivo (Gabizon, 1994). Because free DXR is rapidly and widely redistributed to tissues after systemic administration, it is expected that the pH-sensitive targeted formulation, with their ability to selectively bind the target cells and to efficiently deliver (intracellularly) the encapsulated payload, will have an advantage over the free drug in vivo.

Overall, treatment of human endothelial and tumor cells with peptide-targeted pH-sensitive liposomes containing doxorubicin (SLF3[DXR] pH-sensitive), induces a faster and stronger inhibition of cell growth than the other tested formulations containing doxorubicin (non-targeted pH-sensitive, SL[DXR] pH-sensitive, or peptide-targeted or non-targeted, non-pH sensitive liposomes, SLF3[DXR] and SL[DXR], respectively) (Table 1). Targeted intracellular triggered-doxorubicin release (upon decrease of pH) proved to be a crucial feature for the dramatic improvement of doxorubicin cytostatic activity, when delivered by peptide-targeted pH-sensitive liposomes.

TABLE 1

Cytotoxicity of several formulations of DXR against MDA-MB-435S or HMEC-1 cell lines.

| Time (h) | DXR | SL[DXR] | SLF3[DXR] | SL[DXR] pH-sensitive | SLF3[DXR] pH-sensitive |
|---|---|---|---|---|---|
| | | $IC_{50}$ ($\mu$M) ± SD | | | |
| | | HMEC-1 | | | |
| 1 | 0.434 ± 0.030 | 614.6 ± 0.029 | >300 | 87.66 ± 0.062 | 47.69 ± 0.064 |
| 3 | 0.401 ± 0.059 | 89.16 ± 0.108 | 11.54 ± 7.540 | 12.07 ± 2.541 | 6.688 ± 0.119 |
| 24 | 0.072 ± 0.010 | 31.6 ± 0.661 | 7.2 ± 0.093 | 3.57 ± 0.200 | 0.195 ± 0.049 |
| 48 | 0.058 ± 0.008 | 3.575 ± 0.052 | 0.856 ± 0.091 | 0.03 ± 0.026 | ND |
| | | MDA-MB-435S | | | |
| 1 | 1.608 ± 0.460 | >800 | >300 | >500 | >600 |
| 3 | 1.449 ± 0.270 | >700 | 230.5 ± 0.042 | >400 | 159.0 ± 4.950 |
| 24 | 0.232 ± 0.045 | >700 | 41.24 ± 0.069 | 87.33 ± 0.139 | 3.953 ± 0.263 |
| 48 | 0.113 ± 0.078 | >700 | 25.5 ± 0.049 | 55.2 ± 0.049 | 3.366 ± 0.124 |

Cells were incubated with free DXR or DXR encapsulated in non-targeted or F3-targeted, pH-sensitive or non-pH-sensitive, PEG-grafted liposomes for 1, 3, 24 and 48 h at 37° C. in a 95% humidity and 5% $CO_2$ atmosphere. Afterwards, cells were washed with PBS and incubated with fresh culture medium for a total time of 96 h.
$IC_{50}$ was determined by the MTT proliferation assay.
Data are means ± SD of three independent experiments, each done in triplicate.

REFERENCES

Allen T M. Ligand-targeted therapeutics in anticancer therapy. *Nat Rev Cancer* 2002; 2: 750-763.
Allen T M, Chonn A. Large unilamellar liposomes with low uptake into the reticuloendothelial system. *FEBS Lett* 1987; 223: 42-46.
Bartlett G R. Phosphorus assay in column chromatography. *J Biol Chem* 1959; 234: 466-468.
Boehm T, Folkman J, Browder T, O'Reilly M S. Antiangiogenic therapy of experimental cancer does not induce acquired drug resistance. *Nature* 1997; 390: 404-407.
Bolotin E M C R, Bar L K, Emanuel S N, Lasic D D, Barenholz Y. Ammonium sulphate gradients for efficient and stable remote loading of amphipathic weak bases into liposomes and ligandoliposomes. *J Liposome Res* 1994; 4: 455-479.
Carmeliet P. Angiogenesis in health and disease. *Nat Med* 2003; 9: 653-660.
Christian S, Pilch J, Akerman M E, Porkka K, Laakkonen P, Ruoslahti E. Nucleolin expressed at the cell surface is a marker of endothelial cells in angiogenic blood vessels. *J Cell Biol* 2003; 163: 871-878.
Conner S D, Schmid S L. Regulated portals of entry into the cell. *Nature* 2003; 422: 37-44.
Daleke D L, Hong K, Papahadjopoulos D. Endocytosis of liposomes by macrophages: binding, acidification and leakage of liposomes monitored by a new fluorescence assay. *Biochim Biophys Acta* 1990; 1024: 352-366.
Devy L, de Groot F M, Blacher S, Hajitou A, Beusker P H, Scheeren H W, Foidart J M, Noel A. Plasmin-activated doxorubicin prodrugs containing a spacer reduce tumor growth and angiogenesis without systemic toxicity. *Faseb J* 2004; 18: 565-567.
Drummond D C, Meyer O, Hong K, Kirpotin D B, Papahadjopoulos D. Optimizing liposomes for delivery of chemotherapeutic agents to solid tumors. *Pharmacol Rev* 1999; 51: 691-743.
Drummond D C, Zignani M, Leroux J. Current status of pH-sensitive liposomes in drug delivery. *Prog Lipid Res* 2000; 39: 409-460.
Feron O. Targeting the tumor vascular compartment to improve conventional cancer therapy. *Trends Pharmacol Sci* 2004; 25: 536-542.
Ferrara N, Kerbel R S. Angiogenesis as a therapeutic target. *Nature* 2005; 438: 967-974.
Folkman J. What is the evidence that tumors are angiogenesis dependent? *J Natl Cancer Inst* 1990; 82: 4-6.
Folkman J. Addressing tumor blood vessels. *Nat Biotechnol* 1997; 15: 510.
Folkman J. Angiogenesis: an organizing principle for drug discovery? *Nat Rev Drug Discov* 2007; 6: 273-286.
Folkman J, Ryeom S. Is oncogene addiction angiogenesis-dependent? *Cold Spring Harb Symp Quant Biol* 2005; 70: 389-397.
Fonseca C, Moreira J N, Ciudad C J, Pedroso de Lima M C, Simoes S. Targeting of sterically stabilised pH-sensitive liposomes to human T-leukaemia cells. *Eur J Pharm Biopharm* 2005; 59: 359-366.
Gabizon A, Papahadjopoulos D. The role of surface charge and hydrophilic groups on liposome clearance in vivo. *Biochim Biophys Acta* 1992; 1103: 94-100.
Gabizon A, Catane R, Uziely B, Kaufman B, Safra T, Cohen R, Martin F, Huang A, Barenholz Y. Prolonged circulation time and enhanced accumulation in malignant exudates of doxorubicin encapsulated in polyethylene-glycol coated liposomes. *Cancer Res* 1994; 54: 987-992.
Gatenby R A, Frieden B R. Information dynamics in carcinogenesis and tumor growth. *Mutat Res* 2004; 568: 259-273.
Hajitou A, Pasqualini R, Arap W. Vascular targeting: recent advances and therapeutic perspectives. *Trends Cardiovasc Med* 2006; 16: 80-88.
Hanahan D, Folkman J. Patterns and emerging mechanisms of the angiogenic switch during tumorigenesis. *Cell* 1996; 86: 353-364.
Hashizume H, Baluk P, Morikawa S, McLean J W, Thurston G, Roberge S, Jain R K, McDonald D M. Openings between defective endothelial cells explain tumor vessel leakiness. *Am J Pathol* 2000; 156: 1363-1380.
Hristova E N, Cecco S, Niemela J E, Rehak N N, Elin R J. Analyzer-dependent differences in results for ionized calcium, ionized magnesium, sodium, and pH. *Clin Chem* 1995; 41: 1649-1653.
Ishida T, Okada Y, Kobayashi T, Kiwada H. Development of pH-sensitive liposomes that efficiently retain encapsulated doxorubicin (DXR) in blood. *Int J Pharm* 2006; 309: 94-100.

Lasic D D, Martin F J, Gabizon A, Huang S K, Papahadjopoulos D. Sterically stabilized liposomes: a hypothesis on the molecular origin of the extended circulation times. *Biochim Biophys Acta* 1991; 1070: 187-192.

Maeda H. The enhanced permeability and retention (EPR) effect in tumor vasculature: the key role of tumor-selective macromolecular drug targeting. *Adv Enzyme Regul* 2001; 41: 189-207.

Maeda H, Wu J, Sawa T, Matsumura Y, Hori K. Tumor vascular permeability and the EPR effect in macromolecular therapeutics: a review. *J Control Release* 2000; 65: 271-284.

McDonald D M, Baluk P. Significance of blood vessel leakiness in cancer. *Cancer Res* 2002; 62: 5381-5385.

Mosmann T. Rapid colorimetric assay for cellular growth and survival: application to proliferation and cytotoxicity assays. *J Immunol Methods* 1983; 65: 55-63.

Needham D, Mcintosh T J, Lasic D D. Repulsive interactions and mechanical stability of polymer-grafted lipid membranes. *Biochim Biophys Acta* 1992; 1108: 40-48.

Papahadjopoulos D, Allen T M, Gabizon A, Mayhew E, Matthay K, Huang S K, Lee K D, Woodle M C, Lasic D D, Redemann C, et al. Sterically stabilized liposomes: improvements in pharmacokinetics and antitumor therapeutic efficacy. *Proc Natl Acad Sci USA* 1991; 88: 11460-11464.

Pasqualini R, Arap W, McDonald D M. Probing the structural and molecular diversity of tumor vasculature. *Trends Mol Med* 2002; 8: 563-571.

Porkka K, Laakkonen P, Hoffman J A, Bernasconi M, Ruoslahti E. A fragment of the HMGN2 protein homes to the nuclei of tumor cells and tumor endothelial cells in vivo. *Proc Natl Acad Sci USA* 2002; 99: 7444-7449.

Puri V, Watanabe R, Singh R D, Dominguez M, Brown J C, Wheatley C L, Marks D L, Pagano R E. Clathrin-dependent and -independent internalization of plasma membrane sphingolipids initiates two Golgi targeting pathways. *J Cell Biol* 2001; 154: 535-547.

Rejman J, Bragonzi A, Conese M. Role of clathrin- and caveolae-mediated endocytosis in gene transfer mediated by lipo- and polyplexes. *Mol Ther* 2005; 12: 468-474.

Sapra P, Allen T M. Ligand-targeted liposomal anticancer drugs. *Prog Lipid Res* 2003; 42: 439-462.

Simoes S, Moreira J N, Fonseca C, Duzgunes N, de Lima M C. On the formulation of pH-sensitive liposomes with long circulation times. *Adv Drug Deliv Rev* 2004; 56: 947-965.

Srivastava M, Pollard H B. Molecular dissection of nucleolin's role in growth and cell proliferation: new insights. *Faseb J* 1999; 13: 1911-1922.

Straubinger R M. pH-sensitive liposomes for delivery of macromolecules into cytoplasm of cultured cells. *Methods Enzymol* 1993; 221: 361-376.

Torchilin V P, Omelyanenko V G, Papisov M I, Bogdanov A A, Jr., Trubetskoy V S, Herron J N, Gentry C A. Poly (ethylene glycol) on the liposome surface: on the mechanism of polymer-coated liposome longevity. *Biochim Biophys Acta* 1994; 1195: 11-20.

Woodle M C, Matthay K K, Newman M S, Hidayat J E, Collins L R, Redemann C, Martin F J, Papahadjopoulos D. Versatility in lipid compositions showing prolonged circulation with sterically stabilized liposomes. *Biochim Biophys Acta* 1992; 1105: 193-200.

Wu N Z, Da D, Rudoll T L, Needham D, Whorton A R, Dewhirst M W. Increased microvascular permeability contributes to preferential accumulation of Stealth liposomes in tumor tissue. *Cancer Res* 1993; 53: 3765-3770.

Yuan F, Leunig M, Huang S K, Berk D A, Papahadjopoulos D, Jain R K. Microvascular permeability and interstitial penetration of sterically stabilized (stealth) liposomes in a human tumor xenograft. *Cancer Res* 1994; 54: 3352-3356.

Zalipsky S. Functionalized poly(ethylene glycol) for preparation of biologically relevant conjugates. *Bioconjug Chem* 1995; 6: 150-165.

---

What is claimed:

1. A ligand-targeted delivery system comprising a ligand linked to a support carrying an agent,
   wherein said ligand is a peptide comprising the amino acid sequence of F3 (SEQ ID NO: 1), wherein said support is a pH sensitive liposome,
   wherein the agent is a therapeutic, diagnostic and/or imaging agent, encapsulated, entrapped or intercalated in the support, and
   wherein said liposome is capable of the pH dependent intracellular release of said agent.

2. The ligand-targeted delivery system according to claim 1, wherein said liposome comprises
   dioleoylphosphatidylethanolamine, cholesteryl hemisuccinate and one or more lipids selected from the group consisting of methoxy-poly(ethylene glycol) phosphatidylethanolamine, maleimide-poly(ethylene glycol) phosphatidylethanolamine, N methylpalmitoyloleoylphosphatidylcholine, phosphatidylserine, phosphatidylcholine, palmitoyloleoylphosphatidylcholine, dipalmitoylphosphatidylcholine, distearoylphosphatidylcholine, phosphatidylglycerol and cholesterol.

3. The ligand-targeted delivery system according to claim 1, wherein said liposome comprises
   dioleoylphosphatidylethanolamine, cholesteryl hemisuccinate, fully hydrogenated soy phosphatidylcholine, cholesterol, distearoylphosphatidylethanolamine methoxy(polyethylene glycol) (2000) and distearoylphosphatidylethanolamine maleimide(polyethylene glycol).

4. The ligand-targeted delivery system according to claim 1, wherein said liposome comprises
   dioleoylphosphatidylethanolamine, cholesteryl hemisuccinate, fully hydrogenated soy phosphatidylcholine, cholesterol, distearoylphosphatidylethanolamine methoxy(polyethylene glycol) (2000) and distearoylphosphatidylethanolamine maleimide(polyethylene glycol) at a 4:2:2:2:0.18:0.12 molar ratio.

5. The ligand-targeted delivery system according to claim 1, wherein the therapeutic agent comprises
   a cytotoxic compound, an anti-cancer compound, anti-inflammatory compound, an anti-angiogenic compound, an angiolytic compound, a vascular disrupting compound or a photodynamic therapeutic agent, or combination thereof.

6. The ligand-targeted delivery system according to claim 5, wherein the agent is one or more of the compounds selected from the group consisting of alkylating drugs; cytotoxic antibiotics; antimetabolites; vinca alkaloids; amsacrine; altertarmine; crisantaspase; dacarbazine; temozolomide; hydroxycarbamide (hydroxyurea); pentostatin; platinum compounds; porfimer sodium; procarbazine; razoxane; taxanes; topoisomerase I inhibitors; trastuzumab; tretinoin; SN-38; ET-743; TLK 286; anti-inflammatory agents; antiangiogenic agents or angiolytic agents; ABT-627; Bay 12-9566; Benefin; Bevacizumab; BMC-275291; cartilage-derived inhibitor (CDI); CAI; CD59 complement fragment; CEP-7055; Col 3; Combretastatin A-4; Endostatin (collagenXVIII fragment); Fibronectin fragment; Gro-beta; Halofuginone; Heparinases; Heparin hexasaccharide fragment; HMV833; Human chorionicgonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAbIMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); bisphosphonates; and porphyrins.

7. The ligand-targeted delivery system according to claim 6, wherein
   the alkylating drugs are one or more of cyclophosphamide, chlorambucil, melphalan, busulfan, lomustin, carmustine, chlormethine (mustine), estramustine, treosulfan, thiotepa, or mitobronitol;
   the cytoxic antibotics are one or more of doxorubicin, epirubicin, aclarubicin, idarubicin, daunorubicin, mitoxantrone (mitozantrone), bleomycin, dactinomycin or mitomycin;
   the antimetabolites are one or more of methotrexate, capecitabine, cytarabine, fludarabine, cladribine, gemcitabine, fluorouracil, raltitrexed (tomudex), mercaptopurine, tegafur or tioguanine;
   the vinca alkaloids are one more of vinblastine, vincristine, vindesine, vinorelbine or etoposide;
   the platinum compounds are one or more of carboplatin, cisplatin or oxaliplatin;
   the taxanes are one more of docetaxel or paclitaxel;
   the topoisomerase I inhibitors are one or both of inotecan or topotecan;
   the anti-inflammatory agents are one or more of ibuprofen, aceclofenac, acemetacin, azapropazone, celecoxib, dexketoprofen, diclofenac sodium, diflunisal, cetodolac, fenbufen, fenoprofen, flubiprofen, indomethacin, acetaminocin, piroxicam, rofecoxib, sulindac, tenoxicam, tiaprofenuic acid, aspirin or benorilate;
   the antiangiogenic agents or angiolytic agents are one or more of Angiostatin (plasminogen fragment), antiangiogenic antithrombin III or Angiozyme.

8. The ligand-targeted delivery system according to claim 6, wherein the anti-inflammatory agents are one or more of ibuprofen, aceclofenac, acemetacin, azapropazone, celecoxib, dexketoprofen, diclofenac sodium, diflunisal, cetodolac, fenbufen, fenoprofen, flubiprofen, indomethacin, acetaminocin, piroxicam, rofecoxib, sulindac, tenoxicam, tiaprofenuic acid, aspirin or benorilate.

9. The ligand-targeted delivery system according to claim 1, wherein a spacer is positioned between the ligand and the support.

10. The ligand-targeted delivery system according to claim 8, wherein the spacer comprises a tag that facilitates recovery or identification of the liposome composition.

11. The ligand-targeted delivery system as in one of claims 1 to 6, wherein the agent is doxorubicin.

12. The ligand-targeted delivery system according to claim 1, wherein the agent is a radionuclide or a fluorescent molecule.

* * * * *